(12) United States Patent
Kurata

(10) Patent No.: US 12,298,225 B2
(45) Date of Patent: May 13, 2025

(54) HUMIDITY MEASURING DEVICE

(71) Applicant: SMC CORPORATION, Tokyo (JP)

(72) Inventor: Toshinori Kurata, Tsukubamirai (JP)

(73) Assignee: SMC CORPORATION, Tokyo (JP)

( * ) Notice: Subject to any disclaimer, the term of this patent is extended or adjusted under 35 U.S.C. 154(b) by 377 days.

(21) Appl. No.: 17/841,961

(22) Filed: Jun. 16, 2022

(65) Prior Publication Data

US 2022/0404304 A1    Dec. 22, 2022

(30) Foreign Application Priority Data

Jun. 22, 2021 (JP) ................................. 2021-103308
Apr. 27, 2022 (JP) ................................. 2022-073321

(51) Int. Cl.
*G01N 19/10* (2006.01)
*F24F 11/52* (2018.01)
(Continued)

(52) U.S. Cl.
CPC .............. *G01N 19/10* (2013.01); *F24F 11/52* (2018.01); *G01D 21/02* (2013.01); *G01N 1/2205* (2013.01);
(Continued)

(58) Field of Classification Search
CPC ...... G01N 19/10; G01N 1/2205; G01N 25/66; G01N 27/223; G01N 33/0004; G01N 1/24;
(Continued)

(56) References Cited

U.S. PATENT DOCUMENTS 3,999,706 A    12/1976  Lewis
5,792,938 A *  8/1998  Gokhfeld ............. G01N 27/124
                                                  73/29.02
(Continued)

FOREIGN PATENT DOCUMENTS

JP    6386589 B2    9/2018

OTHER PUBLICATIONS

Partial European Search Report issued Oct. 25, 2022 in European Patent Application No. 22179210.4, 13 pages.
(Continued)

*Primary Examiner* — Nathaniel T Woodward
*Assistant Examiner* — Philip L Cotey
(74) *Attorney, Agent, or Firm* — Oblon, McClelland, Maier & Neustadt, L.L.P.

(57) ABSTRACT

A humidity measuring device is equipped with a temperature and humidity measurement unit including a temperature sensing element that measures temperature and a humidity sensing element that measures humidity, a casing having an accommodating section in which the temperature and humidity measurement unit is accommodated, and a supply tube that supplies a gas at a measurement location into the accommodating section, and a display unit having a display device, and which is fixed to the casing. The display unit further includes a display control unit that controls the display device to thereby cause the display device to display at least one of the humidity of the gas measured by the humidity sensing element, or a dew point temperature of the gas calculated based on the temperature of the gas measured by the temperature sensing element, and the humidity of the gas measured by the humidity sensing element.

11 Claims, 29 Drawing Sheets

(51) Int. Cl.
*G01D 21/02* (2006.01)
*G01N 1/22* (2006.01)
*G01N 25/66* (2006.01)
*G01N 27/22* (2006.01)
*G01N 33/00* (2006.01)
*F24F 110/20* (2018.01)
*G01D 7/00* (2006.01)
*G01D 11/24* (2006.01)
*G01K 13/024* (2021.01)
*G01N 1/24* (2006.01)
*G01N 25/64* (2006.01)
*G08C 17/02* (2006.01)

(52) U.S. Cl.
CPC ........... *G01N 25/66* (2013.01); *G01N 27/223* (2013.01); *G01N 33/0004* (2013.01); *F24F 2110/20* (2018.01); *G01D 7/002* (2013.01); *G01D 11/245* (2013.01); *G01K 13/024* (2021.01); *G01N 1/24* (2013.01); *G01N 25/64* (2013.01); *G01N 33/0062* (2013.01); *G08C 17/02* (2013.01)

(58) Field of Classification Search
CPC ..... G01N 25/64; G01N 33/0062; F24F 11/52; F24F 2110/20; G01D 21/02; G01D 7/002; G01D 11/245; G01K 13/024; G08C 17/02
See application file for complete search history.

(56) References Cited

U.S. PATENT DOCUMENTS

| | | | |
|---|---|---|---|
| 5,873,256 A * | 2/1999 | Denniston | B60H 1/00414 62/271 |
| 8,107,080 B2 * | 1/2012 | Socha | G01N 1/2247 356/438 |
| 2005/0220167 A1 * | 10/2005 | Kanai | G01N 25/68 374/16 |
| 2009/0314053 A1 * | 12/2009 | Rombach | G01N 33/0006 73/1.06 |
| 2010/0154446 A1 * | 6/2010 | Oh | F25D 17/042 62/271 |
| 2012/0042672 A1 * | 2/2012 | Fujihara | F24F 3/14 62/157 |
| 2013/0035869 A1 * | 2/2013 | Minges | G01N 33/0004 73/29.02 |
| 2014/0216135 A1 * | 8/2014 | Minges | G01N 33/0004 73/31.01 |
| 2017/0234845 A1 * | 8/2017 | Worth | G01N 33/0006 73/23.21 |
| 2017/0307244 A1 * | 10/2017 | Elliot | F24F 11/30 |
| 2017/0370862 A1 * | 12/2017 | Isoya | F02D 41/1494 |
| 2019/0011416 A1 * | 1/2019 | Worth | G01N 33/0032 |
| 2019/0257556 A1 * | 8/2019 | Pinet | A47B 73/00 |
| 2020/0300489 A1 * | 9/2020 | Morishita | G05B 15/02 |

OTHER PUBLICATIONS

Notice of Allowance issued Jan. 31, 2025. in U.S. Appl. No. 18/538,366, filed Dec. 13, 2023, (10 pages).

* cited by examiner

43% ▬▬▬ 50%

43% ▬▬▬ 50%

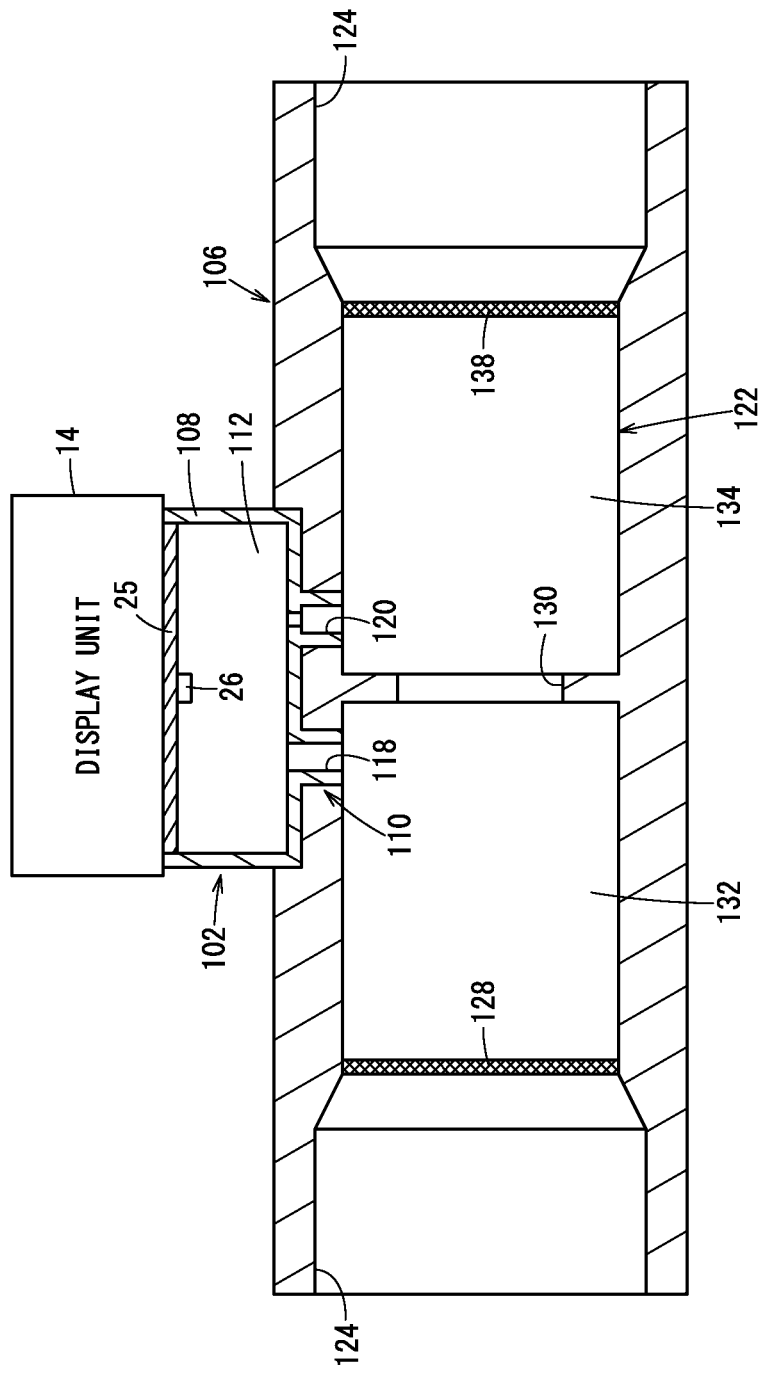

HUMIDITY MEASURING DEVICE

CROSS-REFERENCE TO RELATED APPLICATIONS

This application is based upon and claims the benefit of priority from Japanese Patent Applications No. 2021-103308 filed on Jun. 22, 2021 and No. 2022-073321 filed on Apr. 27, 2022, the contents all of which are incorporated herein by reference.

BACKGROUND OF THE INVENTION

Field of the Invention

The present invention relates to a humidity measuring device that measures the humidity of a gas.

Description of the Related Art

A humidity measuring device is disclosed in JP 6386589 B2. In such a humidity measuring device, the humidity of intake air that flows through a main air passage is measured. An insertion hole is provided in a main air passage wall of the main air passage. The humidity measuring device is inserted into the insertion hole.

SUMMARY OF THE INVENTION

The humidity measuring device disclosed in JP 6386589 B2 does not include a display device on which the humidity of the gas measured by the humidity measuring device is displayed. Thus, a problem arises in that the user is incapable of confirming the humidity of the gas measured by the humidity measuring device.

The present invention has the object of solving the aforementioned problem.

An aspect of the present invention is characterized by a humidity measuring device configured to measure humidity of a gas, including a measurement unit including a temperature sensing element configured to measure temperature, and a humidity sensing element configured to measure humidity, a casing including an accommodating section in which the measurement unit is accommodated, and a display unit including a display device, and which is fixed to the casing, wherein the display unit further includes a display control unit configured to control the display device to thereby cause the display device to display at least one of the humidity of the gas measured by the humidity sensing element, or a dew point temperature of the gas calculated based on both the temperature of the gas measured by the temperature sensing element and the humidity of the gas measured by the humidity sensing element.

According to the present invention, the user is capable of confirming at least one of the dew point temperature or the humidity measured by the humidity measuring device.

The above and other objects, features, and advantages of the present invention will become more apparent from the following description when taken in conjunction with the accompanying drawings, in which preferred embodiments of the present invention are shown by way of illustrative example.

BRIEF DESCRIPTION OF THE DRAWINGS

FIGS. 10A and 10B are diagrams showing experimental environments in which experiments were conducted by the present inventors and the like;
FIG. 29 is a view showing the humidity measuring device.

DESCRIPTION OF THE INVENTION

First Embodiment

Figure 1:
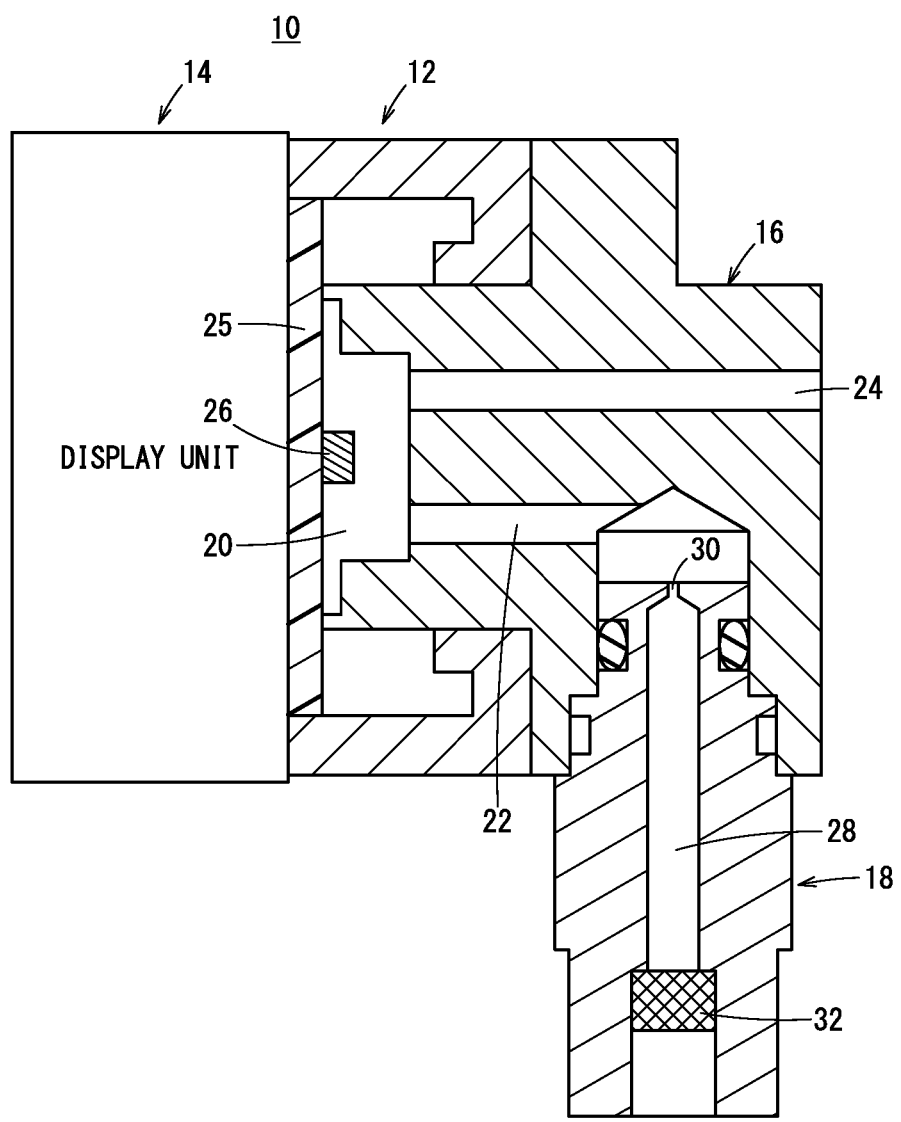
FIG. 1 is a view showing a humidity measuring device.

FIG. 1 is a view showing a humidity measuring device 10. The humidity measuring device 10 includes a casing 12 and a display unit 14. In FIG. 1, a cross-sectional view of the casing 12 is shown. In FIG. 1, a schematic diagram of the display unit 14 is shown. The humidity measuring device 10 measures a relative humidity of the gas and a temperature of the gas. Hereinafter, the relative humidity will be referred to simply as a humidity.

The casing 12 includes a main body portion 16 and a connecting portion 18. The main body portion 16 includes an accommodating section 20 disposed in the interior of the main body portion 16. The accommodating section 20 is a space formed inside the main body portion 16. The main body portion 16 includes a supply tube 22 disposed in the interior of the main body portion 16. The main body portion 16 includes a discharge tube 24 disposed in the interior of the main body portion 16. The supply tube 22 is connected to the accommodating section 20. The discharge tube 24 is connected to the accommodating section 20. As shown in FIG. 1, an opening of the discharge tube 24 in the accommodating section 20 is arranged at a position that is offset, with respect to an opening of the supply tube 22 in the accommodating section 20, in a radial direction of the opening of the supply tube 22. Gas is supplied from the supply tube 22 into the accommodating section 20. The gas that is supplied into the accommodating section 20 is discharged from the discharge tube 24 into the atmosphere.

The humidity measuring device 10 includes an electronic circuit board 25. The electronic circuit board 25 is arranged between the main body portion 16 and the display unit 14. A temperature and humidity measurement unit 26 is mounted on the electronic circuit board 25. The temperature and humidity measurement unit 26 is accommodated in the accommodating section 20. The temperature and humidity measurement unit 26 is an electronic component in which a temperature sensing element and a humidity sensing element are mounted in one single integrated circuit. The temperature sensing element measures the temperature of the gas in the accommodating section 20. The humidity sensing element measures the humidity of the gas in the accommodating section 20. The temperature and humidity measurement unit 26 corresponds to a measurement unit of the present invention. The temperature and humidity measurement unit 26 outputs to the display unit 14 the temperature and humidity of the gas that were measured.

The connecting portion 18 is mounted on the main body portion 16. The connecting portion 18 includes a connecting tube 28 in the interior of the connecting portion 18. Gas is capable of flowing between the connecting tube 28 and the supply tube 22 of the main body portion 16.

The connecting tube 28 includes an orifice 30. A filter 32 is mounted in the connecting tube 28. The filter 32 is made of metal. In the connecting tube 28, the orifice 30 is arranged at a position in closer proximity to the main body portion 16 than the position where the filter 32 is mounted. More specifically, the orifice 30 is arranged at a position in closer proximity to the accommodating section 20 than the position where the filter 32 is mounted. In the orifice 30, the cross-sectional area of a minimum diameter portion of the hole of the orifice 30 is smaller than the cross-sectional area of the discharge tube 24. Therefore, a flow path resistance of a pathway (hereinafter, referred to as a discharge pathway) through which the gas from the accommodating section 20 is discharged is smaller than a flow path resistance of a pathway (hereinafter, referred to as a supply pathway) through which the gas is supplied to the accommodating section 20. Consequently, the pressure of the gas inside the accommodating section 20 becomes the atmospheric pressure. The temperature and humidity measurement unit 26, which is accommodated in the accommodating section 20, measures the temperature of the gas under atmospheric pressure. The temperature and humidity measurement unit 26, which is accommodated in the accommodating section 20, also measures the humidity of the gas under atmospheric pressure.

Figure 2:
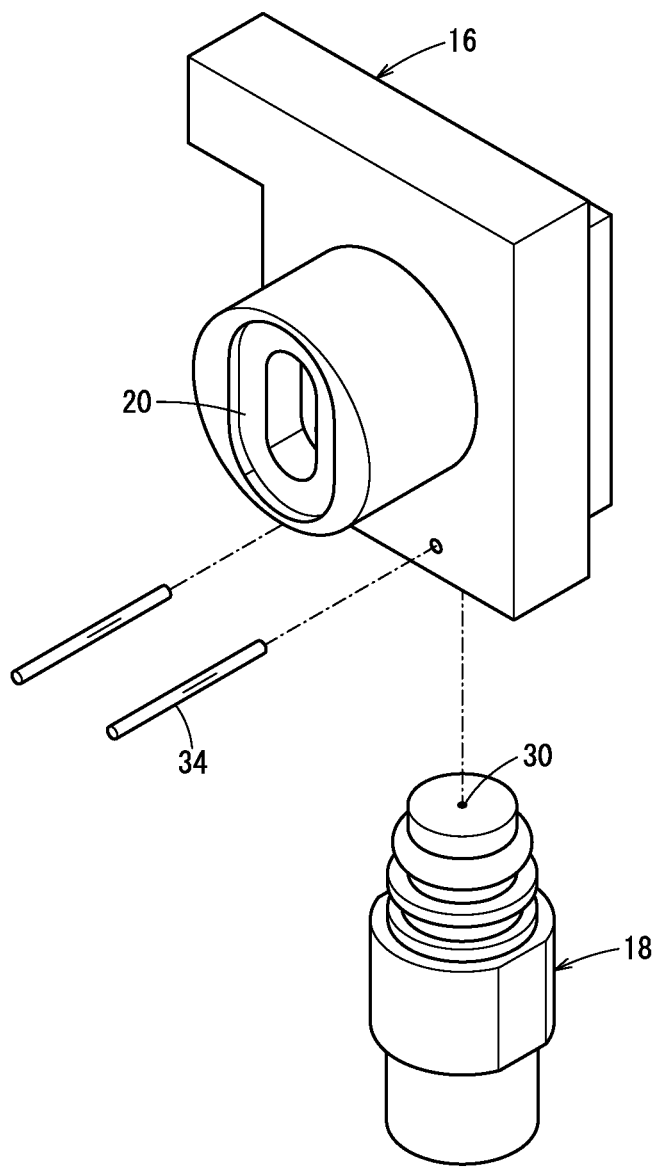
FIG. 2 is a perspective view of a casing.

FIG. 2 is a perspective view of the casing 12. The connecting portion 18 is fixed to the main body portion 16 by connecting pins 34. The user can pull out the connecting pins 34. In a state in which the connecting pins 34 are pulled out from the main body portion 16 and the connecting portion 18, the user is capable of detaching the connecting portion 18 from the main body portion 16. The connecting portion 18 is detached from the main body portion 16 in a state in which the filter 32 is mounted in the connecting portion 18. Consequently, the user is capable of easily replacing the filter 32 of the humidity measuring device 10.

Figure 3:
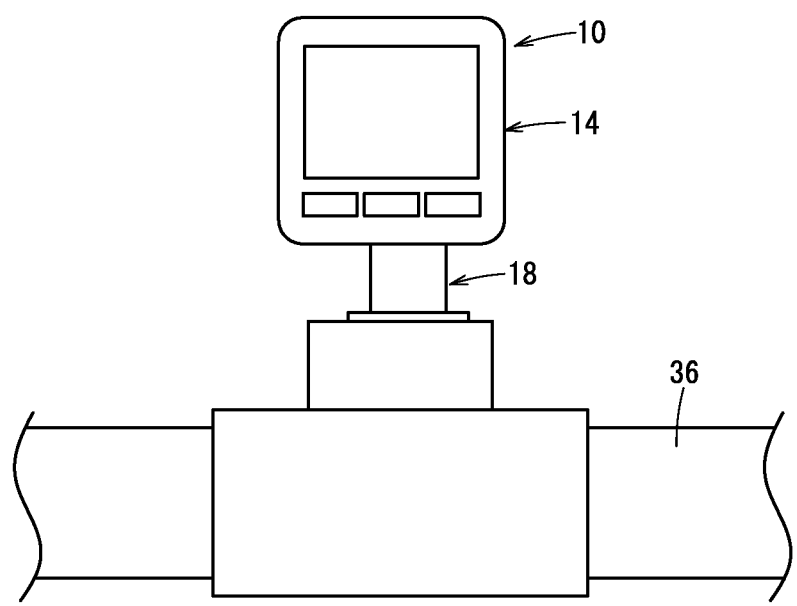
FIG. 3 is a view showing an example of installing the humidity measuring device.

FIG. 3 is a view showing an example of installing the humidity measuring device 10. The humidity measuring device 10 is installed in a tube 36. A compressed gas flows in the interior of the tube 36. The compressed gas is a gas in which the pressure of the gas is higher than atmospheric pressure. Hereinafter, even if the gas is a compressed gas, the gas may be simply referred to as a gas.

The temperature, the humidity, and the dew point temperature of the gas vary depending on the pressure of the gas. The temperature, the humidity, and the dew point temperature of a compressed gas in which the pressure of the gas is higher than atmospheric pressure may be described as a temperature under the pressure of the gas, a humidity under the pressure of the gas, and a dew point temperature under the pressure of the gas. The temperature, the humidity, and the dew point temperature of a gas in which the pressure of the gas is equivalent to the atmospheric pressure may be described as a temperature under atmospheric pressure of the gas, a humidity under atmospheric pressure of the gas, and a dew point temperature under atmospheric pressure of the gas.

The humidity measuring device 10 measures the humidity and the temperature of the gas that flows through the interior of the tube 36. The connecting portion 18 of the humidity measuring device 10 is inserted into a non-illustrated insertion hole provided in the tube 36. Due to this feature, a portion of the gas that flows into the interior of the tube 36 passes through the connecting tube 28 of the connecting portion 18, and the supply tube 22 of the main body portion 16, and is supplied to the accommodating section 20. The gas that flows through the interior of the tube 36 is a gas that is dehumidified by a dehumidifying device 38, which will be described next.

Figure 4:
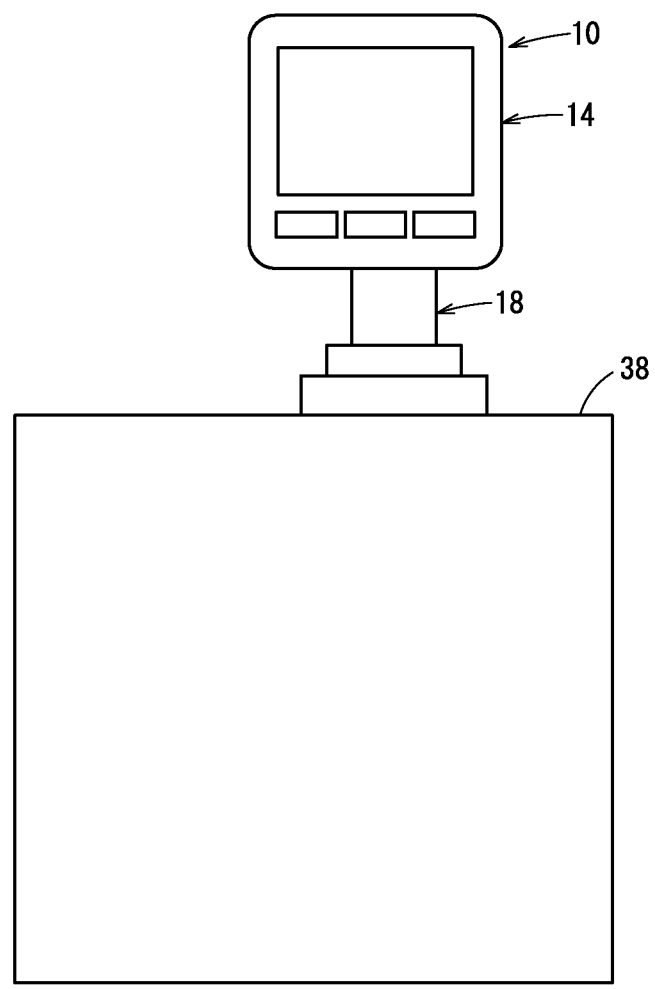
FIG. 4 is a view showing an example of installing the humidity measuring device.

FIG. 4 is a view showing an example of installing the humidity measuring device 10. The humidity measuring device 10 may be installed in the dehumidifying device 38. The dehumidifying device 38 removes moisture in the gas that passes through the interior of the dehumidifying device 38. The humidity measuring device 10 measures the humidity and the temperature of the compressed gas that is discharged from the dehumidifying device 38.

Figure 5:
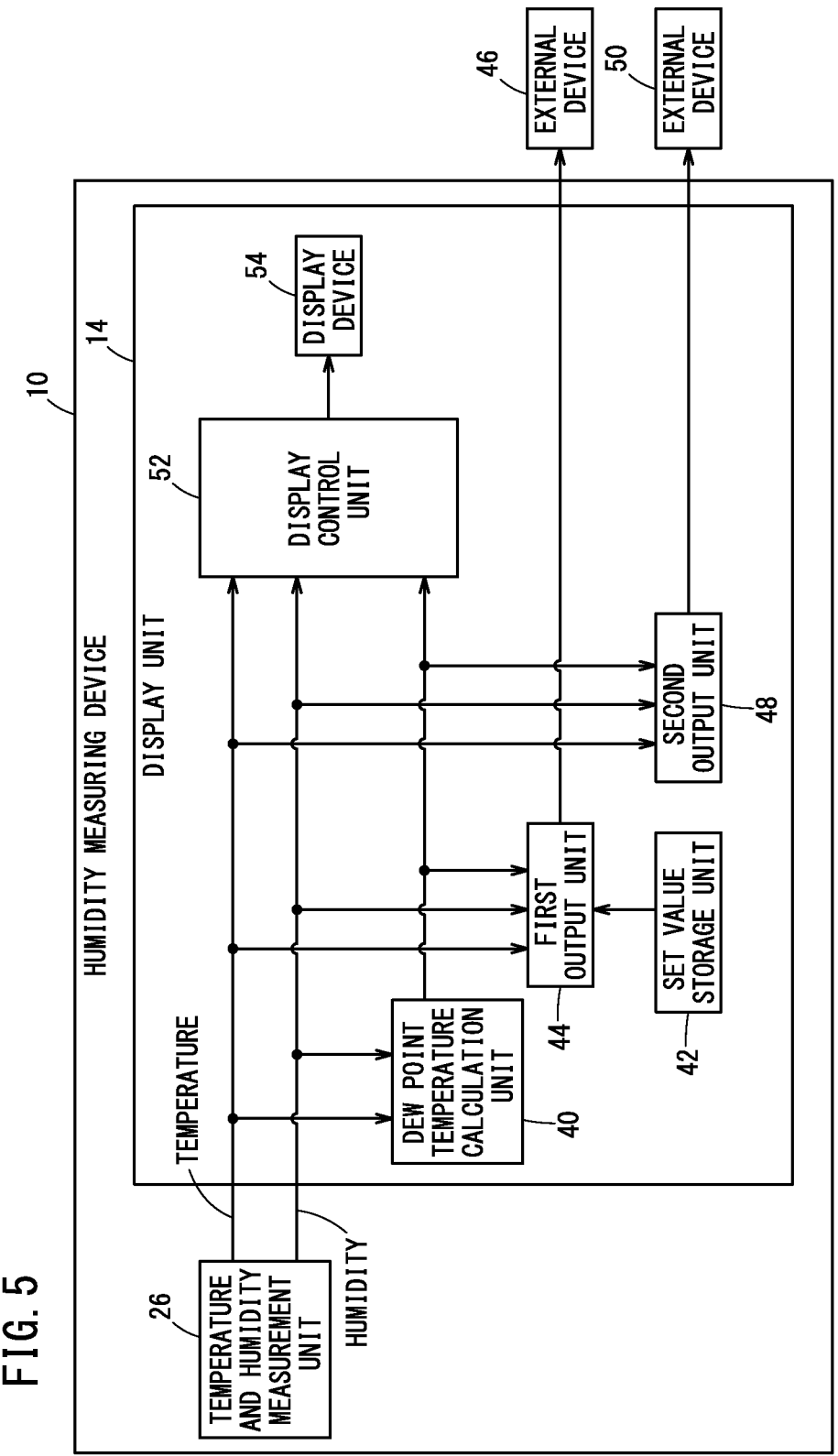
FIG. 5 is a control block diagram of the humidity measuring device.

As shown in FIG. 1, the display unit 14 is fixed to the main body portion 16 of the casing 12. FIG. 5 is a control block diagram of the humidity measuring device 10. With reference to the control block diagram of FIG. 5, a description will be given concerning the configuration of the display unit 14.

The display unit 14 includes a dew point temperature calculation unit 40, a set value storage unit 42, a first output unit 44, a second output unit 48, a display control unit 52, and a display device 54.

The dew point temperature calculation unit 40 calculates the dew point temperature under atmospheric pressure of the gas, based on the temperature of the gas measured by the temperature and humidity measurement unit 26, and the humidity of the gas measured by the temperature and humidity measurement unit 26. The dew point temperature calculation unit 40 outputs the calculated dew point temperature to the first output unit 44, the second output unit 48, and the display control unit 52.

Hereinafter, the "temperature of the gas measured by the temperature and humidity measurement unit 26" may be referred to as a "measured temperature". The "humidity of the gas measured by the temperature and humidity measurement unit 26" may be referred to as a "measured humidity". The "dew point temperature of the gas calculated by the dew point temperature calculation unit 40" may be referred to as a "calculated dew point temperature".

The set value storage unit 42 stores a set temperature, a set humidity, and a set dew point temperature. The set temperature, the set humidity, and the set dew point temperature are input to the first output unit 44, as will be described later. The set temperature, the set humidity, and the set dew point temperature may be values set by the user of the humidity measuring device 10. The set temperature, the set humidity, and the set dew point temperature may also be values set by a manufacturer of the humidity measuring device 10 at a time of shipment of the humidity measuring device 10.

The first output unit 44 compares the set temperature with the measured temperature. The first output unit 44 outputs a comparison result (hereinafter, such a result may be referred to as a temperature comparison result) to an external device 46. The temperature comparison result may be information numerically indicating a difference between the set temperature and the measured temperature. The temperature comparison result may be information indicating a highness or lowness of the measured temperature with respect to the set temperature.

The first output unit 44 compares the set humidity with the measured humidity. The first output unit 44 outputs a comparison result (hereinafter, such a result may be referred to as a humidity comparison result) to the external device 46. The humidity comparison result may be information numerically indicating a difference between the set humidity and the measured humidity. The humidity comparison result may be information indicating a highness or lowness of the measured humidity with respect to the set humidity.

The first output unit 44 compares the set dew point temperature with the calculated dew point temperature. The first output unit 44 outputs a comparison result (hereinafter, such a result may be referred to as a dew point temperature comparison result) to the external device 46. The dew point temperature comparison result may be information numerically indicating a difference between the set dew point temperature and the calculated dew point temperature. The dew point temperature comparison result may be information numerically indicating a highness or lowness of the calculated dew point temperature with respect to the set dew point temperature.

The second output unit 48 outputs the measured temperature to an external device 50. The second output unit 48 outputs the measured humidity to the external device 50. The second output unit 48 outputs the calculated dew point temperature to the external device 50. The external device 50 may be the same device as the external device 46. The external device 50 may also be a device that is different from the external device 46.

The display control unit 52 controls the display device 54 to thereby cause information concerning the measured temperature to be displayed on the display device 54. The display control unit 52 controls the display device 54 to thereby cause information concerning the measured humidity to be displayed on the display device 54. The display control unit 52 controls the display device 54 to thereby cause information concerning the calculated dew point temperature to be displayed on the display device 54. The display control unit 52 may control the display device 54 to thereby cause at least one of the information concerning the measured temperature, the information concerning the measured humidity, or the information concerning the calculated dew point temperature to be displayed on the display device 54. The units of the measured temperature, the calculated dew point temperature, the set temperature, and the set dew point temperature are in units of "° C.".

Figure 6:
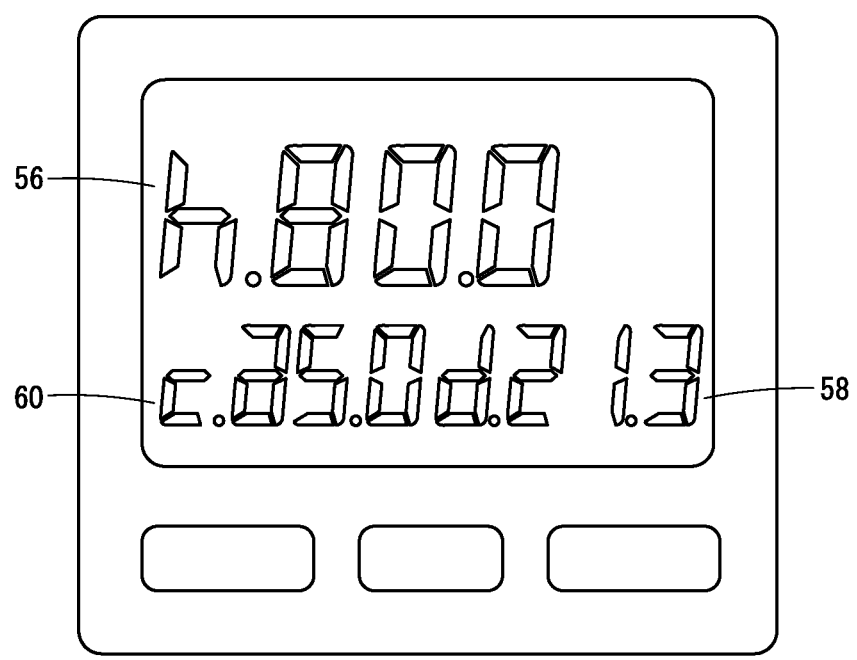
FIG. 6 is a view showing an exemplary display of a display device.

FIG. 6 is a view showing an exemplary display of the display device 54. The display device 54 includes a humidity display region 56. The measured humidity is displayed numerically in the humidity display region 56. The display device 54 includes a dew point temperature display region 58. The calculated dew point temperature is displayed numerically in the dew point temperature display region 58. The display device 54 includes a temperature display region 60. The measured temperature is displayed numerically in the temperature display region 60.

Figure 7A:
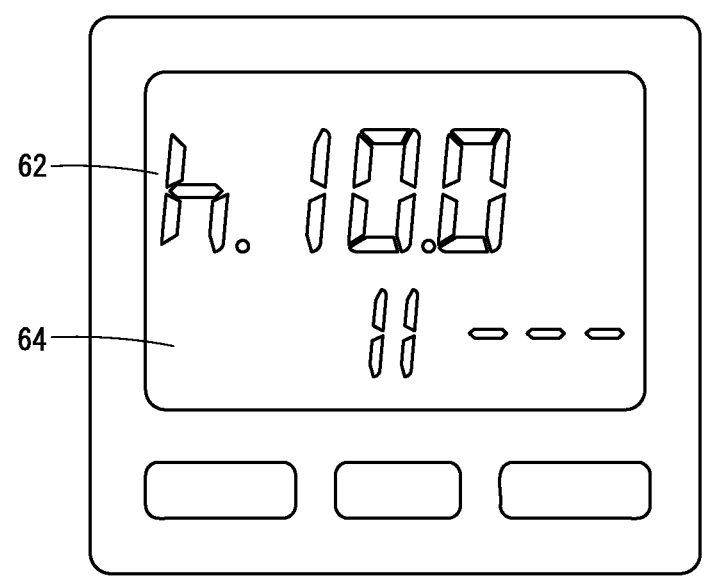
FIGS. 7A and 7B are views showing exemplary displays of the display device.
Figure 7B:
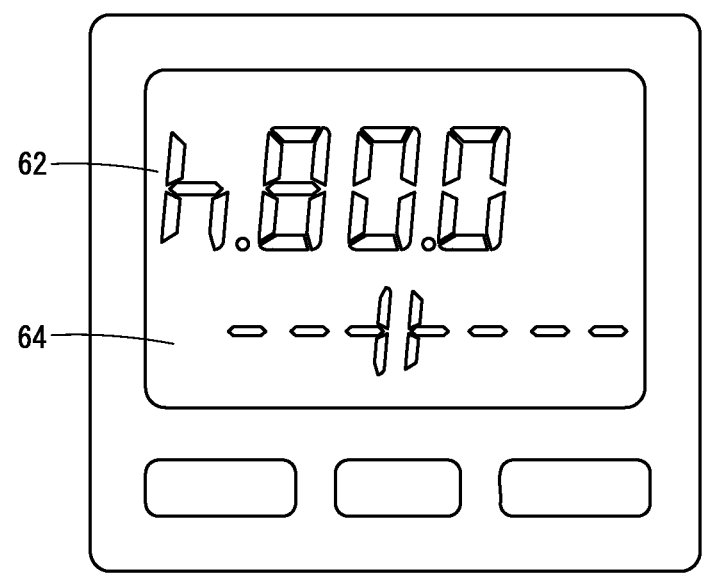

FIGS. 7A and 7B are views showing exemplary displays of the display device 54. The exemplary displays of the display device 54 shown in FIGS. 7A and 7B are exemplary displays that differ from the exemplary display of the display device 54 shown in FIG. 6. The display device 54 includes a humidity display region 62. The measured humidity is displayed numerically in the humidity display region 62. The display device 54 includes a dew point temperature display region 64. The two slashes "//" shown near the center of the dew point temperature display region 64 shown in FIGS. 7A and 7B indicate a position where the calculated dew point temperature is 0° C. In the case that the calculated dew point temperature is negative, then as shown in FIG. 7A, bars (g-segments) "-" are displayed only on the right side of the slashes "//". In the case that the calculated dew point temperature is positive, then as shown in FIG. 7B, bars (g-segments) "-" are displayed such that they extend to the left side of the slashes "//". In the dew point temperature display region 64, the more that the bars (g-segments) "-" extend into the left side, the higher the calculated dew point temperature that is displayed by the display device 54 is.

Figure 8A:
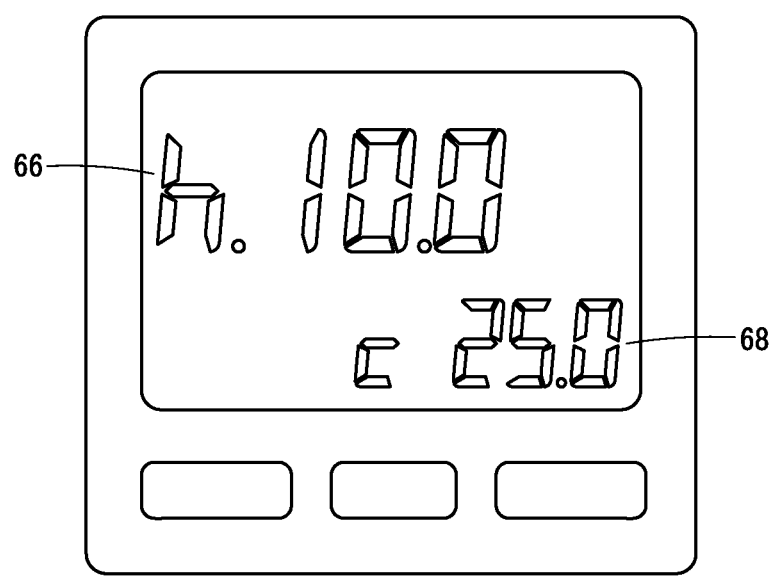
FIGS. 8A and 8B are views showing exemplary displays of the display device.
Figure 8B:
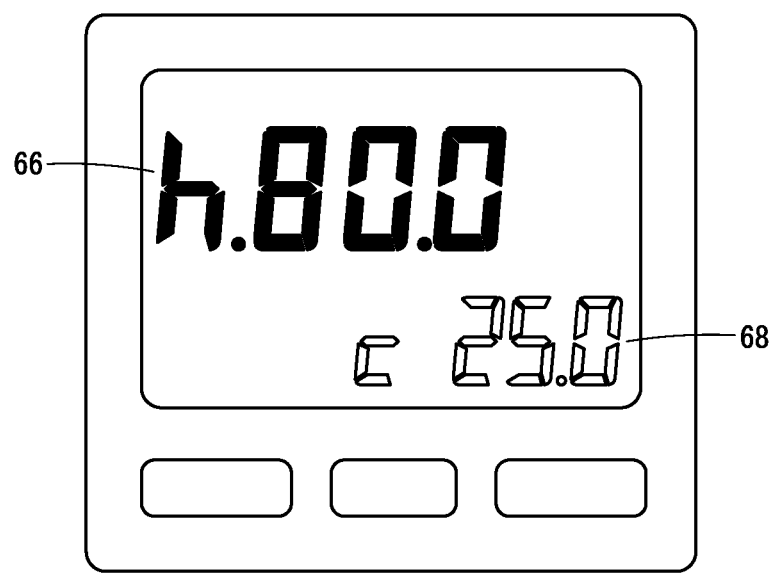

FIGS. 8A and 8B are views showing exemplary displays of the display device 54. The exemplary displays of the display device 54 shown in FIGS. 8A and 8B are exemplary displays that differ from the exemplary displays of the display device 54 shown in FIG. 6 and FIGS. 7A and 7B. The display device 54 includes a humidity display region 66. The measured humidity is displayed numerically in the humidity display region 66. The display device 54 includes a temperature display region 68. The measured temperature is displayed numerically in the temperature display region 68. The display device 54 indicates the calculated dew point temperature by a color of the numbers displayed in the humidity display region 66. In the case that the calculated dew point temperature is negative, the display device 54 displays the numbers in the humidity display region 66 in blue. In the case that the calculated dew point temperature is positive, the display device 54 displays the numbers in the humidity display region 66 in red. The colors of the numbers displayed in the humidity display region 66 described above are given by way of example, and the information concerning the calculated dew point temperature may be displayed in different colors.

Within the display unit 14, the respective constituent features thereof except for the display device 54 are realized by a non-illustrated microcontroller. By a non-illustrated computation processing device provided in the microcontroller executing programs stored in a non-illustrated memory provided on the microcontroller, the functions of the dew point temperature calculation unit 40, the first output unit 44, the second output unit 48, and the display control unit 52 are realized. Further, the set value storage unit 42 is realized by securing a storage region in which respective set values are stored in a portion of the memory.

Moreover, within the display unit 14, the respective constituent features thereof excluding the display device 54 may be configured by integrated circuits such as a non-illustrated FPGA (Field Programmable Gate Array), an ASIC (application specific integrated circuit), or the like.

Concerning the Connection Between the Supply Tube and the Accommodating Section, and the Connection Between the Discharge Tube and the Accommodating Section According to the present embodiment, as shown in FIG. 1, the opening of the discharge tube 24 in the accommodating section 20 is arranged at a position that is offset with respect to an opening of the supply tube 22 in the accommodating section 20. Consequently, the gas that has flowed into the accommodating section 20 from the supply tube 22 is diffused or spread out inside the accommodating section 20, and thereafter, is discharged from the discharge tube 24.

Figure 9A:
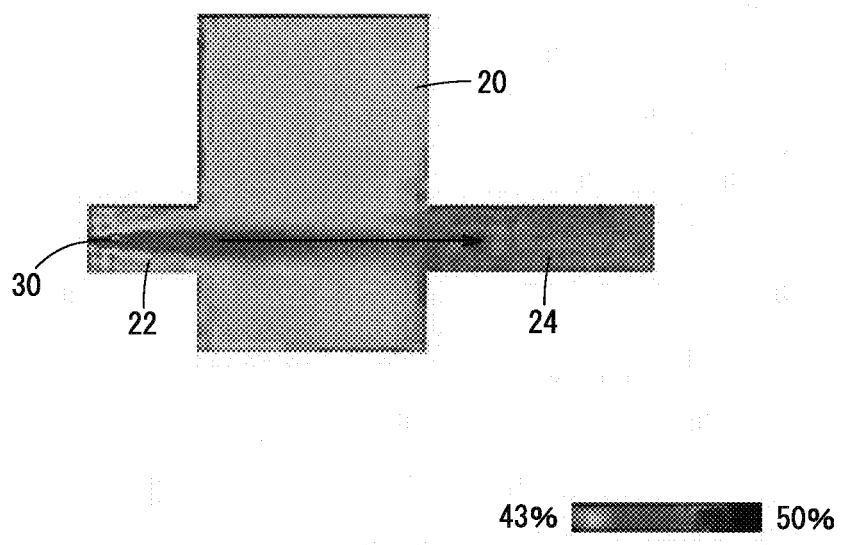
FIGS. 9A and 9B are diagrams showing simulation results.
Figure 9B:
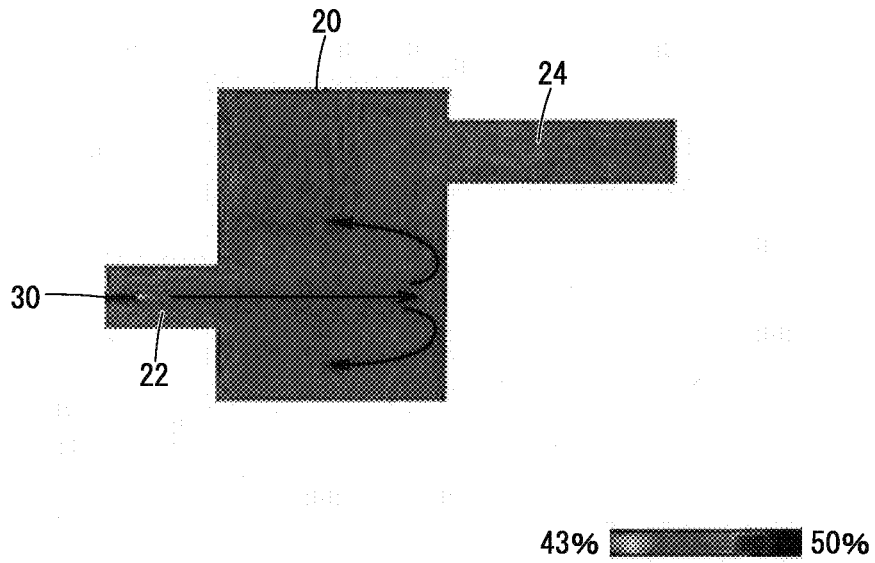

Using a computer, the present inventors have carried out simulations concerning the distribution of the humidity of the gas in the interior of the accommodating section 20. FIGS. 9A and 9B are diagrams showing simulation results. FIG. 9A shows a simulation result in a Comparative Example 1. In Comparative Example 1, the direction in which the gas flows in from the supply tube 22 into the accommodating section 20, and the direction in which the gas flows out from the accommodating section 20 into the discharge tube 24 are positioned mutually on a straight line with each other. FIG. 9B shows a simulation result in a Comparative Example 2. In Comparative Example 2, an opening of the discharge tube 24 in the accommodating section 20 is arranged at a position that is offset, with respect to the opening of the supply tube 22 in the accommodating section 20, in a radial direction of the opening of the supply tube 22. Owing to this feature, in Comparative Example 2, the direction in which the gas flows from the supply tube 22 into the accommodating section 20, and the direction in which the gas flows out from the accommodating section 20 into the discharge tube 24 are positioned mutually on different straight lines.

In the simulations of Comparative Example 1 and Comparative Example 2, the diameter of the hole of the orifice 30 was set to 0.2 mm. In the simulations of Comparative Example 1 and Comparative Example 2, the humidity of the gas that flows into the accommodating section 20 was set to 50%. In the simulations of Comparative Example 1 and Comparative Example 2, the flow rate of the gas that flows into the accommodating section 20 was set to 1 L/min.

In Comparative Example 1, the gas that has flowed into the accommodating section 20 from the supply tube 22 is discharged from the discharge tube 24 without being diffused or spread out inside the accommodating section 20. Therefore, in the simulation in Comparative Example 1, as shown in FIG. 9A, the distribution of the humidity of the gas in the accommodating section 20 is not uniform. On the other hand, in Comparative Example 2, the gas that has flowed into the accommodating section 20 from the supply tube 22 impinges against the side surface of the accommodating section 20, and after being diffused or spread out inside the accommodating section 20, is discharged from the discharge tube 24. Therefore, in the simulation in Comparative Example 2, as shown in FIG. 9B, the distribution of the humidity of the gas in the accommodating section 20 is substantially uniform.

From these simulation results, it was shown that the gas that flows into the accommodating section 20 was diffused or spread out more widely in Comparative Example 2 than in Comparative Example 1.

Figure 10A:
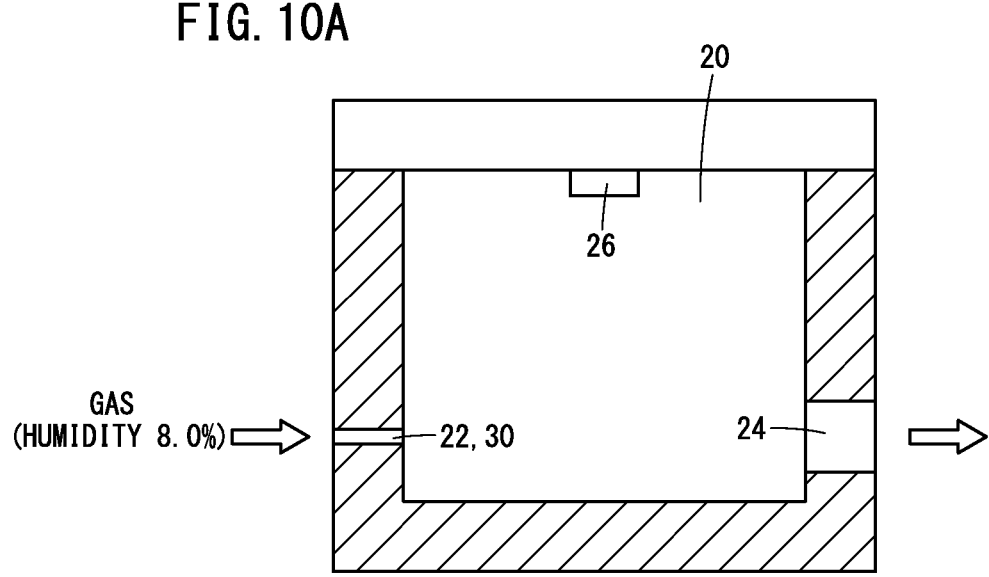
Figure 10B:
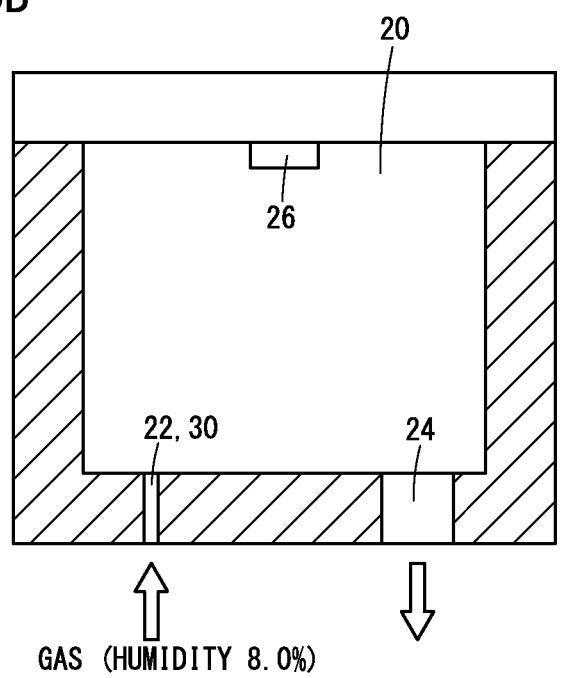

The present inventors conducted experiments concerning the accuracy in measuring the humidity of the gas by the temperature and humidity measurement unit 26. FIGS. 10A and 10B are diagrams showing experimental environments in which experiments were conducted by the present inventors. FIG. 10A shows the experimental environment in a Comparative Example 3. In Comparative Example 3, the direction in which the gas flows in from the supply tube 22 into the accommodating section 20, and the direction in which the gas flows out from the accommodating section 20 into the discharge tube 24 are positioned mutually on a straight line with each other. FIG. 10B shows the experimental environment in a Comparative Example 4. In Comparative Example 4, an opening of the discharge tube 24 in the accommodating section 20 is arranged at a position that is offset, with respect to the opening of the supply tube 22 in the accommodating section 20, in a radial direction of the opening of the supply tube 22. Owing to this feature, in Comparative Example 4, the direction in which the gas flows from the supply tube 22 into the accommodating section 20, and the direction in which the gas flows out from the accommodating section 20 into the discharge tube 24 are positioned mutually on different straight lines. In these experiments, a dry gas (with a humidity of 8.0%) was allowed to flow into the accommodating section 20 which is in a normal humidity state (a humidity of 25.0%).

In the experimental environment in Comparative Example 3 shown in FIG. 10A, the humidity measured by the temperature and humidity measurement unit 26 was 10.3%. A measurement error of the humidity (10.3%) that was measured by the temperature and humidity measurement unit 26 with respect to the humidity (8.0%) of the gas that was made to flow into the accommodating section 20 was +2.3%. In the experimental environment in Comparative Example 4 shown in FIG. 10B, the humidity measured by the temperature and humidity measurement unit 26 was 8.3%. A measurement error of the humidity (8.3%) that was measured by the temperature and humidity measurement unit 26 with respect to the humidity (8.0%) of the gas that was made to flow into the accommodating section 20 was +0.3%.

From these experimental results, it was shown that the accuracy in measuring the humidity of the gas by the temperature and humidity measurement unit 26 is more improved in Comparative Example 4 than in Comparative Example 3.

Concerning the Orifice

In the humidity measuring device 10 according to the present embodiment, because the connecting tube 28 includes the orifice 30, the flow path resistance of the gas discharge pathway of the accommodating section 20 is smaller than the flow path resistance of the gas supply pathway of the accommodating section 20. Consequently, the pressure of the gas inside the accommodating section 20 becomes the atmospheric pressure. Instead of the orifice 30, a structure may be considered in which the connecting tube 28 includes a pressure reducing valve. The pressure reducing valve, by releasing a portion of the gas that passes through the connecting tube 28 into the atmosphere, is capable of adjusting the pressure of the gas supplied to the accommodating section 20 to be equivalent to the atmospheric pressure. The structure of the orifice 30 is simpler in comparison with that of the pressure reducing valve. In the humidity measuring device 10 according to the present embodiment, since the connecting tube 28 includes the orifice 30 instead of a pressure reducing valve, the structure of the humidity measuring device 10 can be simplified.

The filter 32 that is mounted in the connecting tube 28 acts as a resistance to the gas that passes through the filter 32. Therefore, it may be considered that the filter 32 increases the flow path resistance of the supply pathway. Normally, the filter 32 is designed in a manner so that, while the filter 32 removes foreign material in the gas that passes through the filter 32, the resistance with respect to the gas that passes through the filter 32 is as small as possible. In order to generate a flow path resistance that is equivalent to the flow path resistance due to the orifice 30 in the filter 32, it is necessary to mount the filter 32 in the connecting tube 28, which is considerably longer in comparison to the axial length of the hole of the orifice 30. In the humidity measuring device 10 according to the present embodiment, because the orifice 30 increases the flow path resistance of the supply path, the humidity measuring device 10 can be made smaller in scale.

Compared to a case in which the filter 32 causes the flow path resistance of the supply pathway to increase, in the case of the orifice 30 causing the flow path resistance of the supply pathway to increase, the flow velocity of the gas that flows into the accommodating section 20 becomes higher. As the flow velocity of the gas that flows into the accommodating section 20 becomes higher, the gas is diffused or spread out over a wider range when the gas collides against the side surface of the accommodating section 20. As the flow velocity of the gas that flows into the accommodating section 20 becomes higher, the time until the gas that flows into the accommodating section 20 and thereafter collides against the side surface of the accommodating section 20 becomes shortened, and the gas is diffused or spread out more rapidly.

Therefore, compared to a case in which the filter 32 causes the flow path resistance of the supply pathway to increase, in the case of the orifice 30 causing the flow path resistance of the supply pathway to increase, the gas that has flowed into the accommodating section 20 is diffused or spread out more rapidly and over a wider range inside the accommodating section 20. As a result, compared to the case in which the filter 32 causes the flow path resistance of the supply pathway to increase, in the case of the orifice 30 causing the flow path resistance of the supply pathway to increase, with respect to changes in the temperature and humidity or the like of the target gas to be measured, the response speed of the measurement result of the target gas to be measured by the temperature and humidity measurement unit 26 is improved.

Figure 11A:
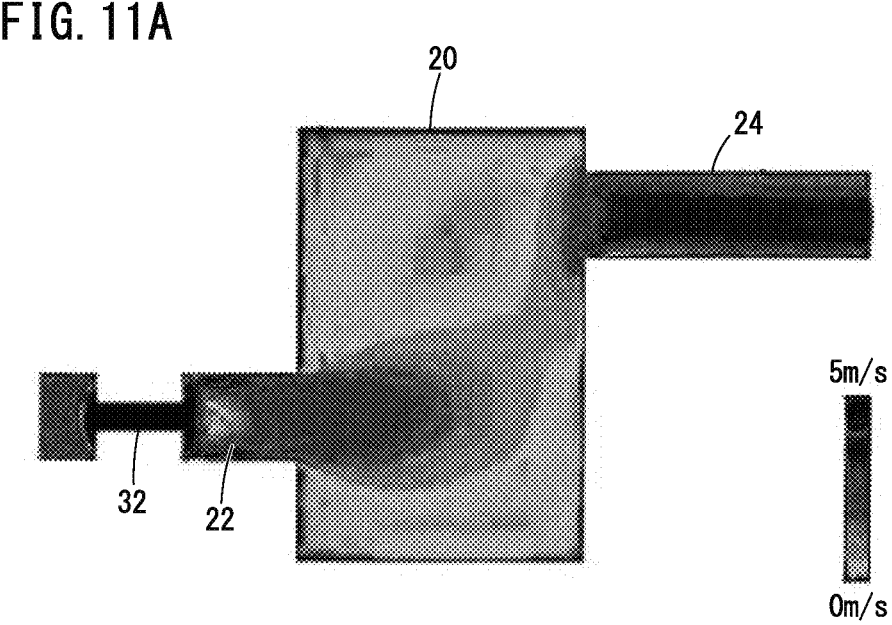
FIGS. 11A and 11B are diagrams showing simulation results.
Figure 11B:
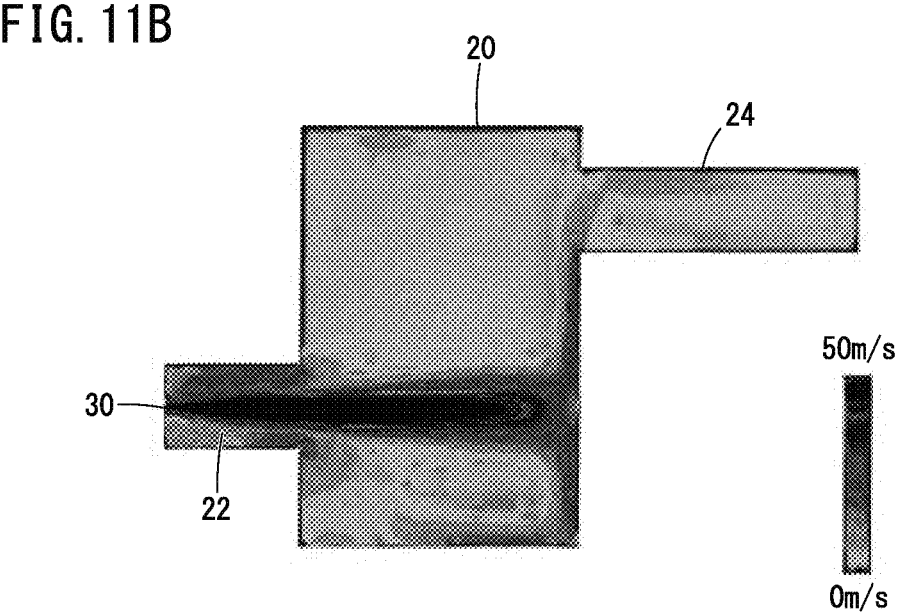

Using a computer, the present inventors have carried out simulations concerning the flow rate of the gas that flows into the accommodating section 20. FIGS. 11A and 11B are diagrams showing simulation results. FIG. 11A is a simulation result in the case that the filter 32 causes the flow path resistance of the supply pathway to increase. FIG. 11B is a simulation result in the case that the orifice 30 causes the flow path resistance of the supply pathway to increase.

In these simulations, an inner diameter of the supply tube 22 was set to 3 mm. In these simulations, the inner diameter of the tube in a portion where the filter 32 is provided was set to 1 mm, and an outer diameter of the filter 32 was also set to 1 mm. In these simulations, the length of the filter 32 was set to 4 mm. In these simulations, an inner diameter of the hole of the orifice 30 was set to 0.2 mm. In these simulations, an axial length of the hole of the orifice 30 was set to 0.2 mm. In these simulations, the humidity of the gas that flows into the accommodating section 20 was set to 50%. In these simulations, the flow rate of the gas that flows into the accommodating section 20 was set to 1 L/min.

In the case that the filter 32 causes the flow path resistance of the supply pathway to increase, then as shown in FIG. 11A, the flow rate of the gas that passes through the filter 32 is high, but the flow rate of the gas after having passed through the filter 32 is low. The reason why the flow velocity of the gas after having passed through the filter 32 decreases in this manner, notwithstanding the fact that the flow velocity of the gas while passing through the filter 32 is high, is as follows.

At an inlet portion where the gas flows into the filter 32, since the gas flows into the filter 32 (having an outer diameter of 1 mm) from the supply tube 22 (having an inner diameter 3 mm), the flow velocity of the gas becomes higher. In the interior of the filter 32, as the flow velocity of the gas becomes higher, the flow path resistance of the filter 32 with respect to the gas increases. Therefore, while passing through the filter 32, the gas diffuses (spreads out) from a location in the interior of the filter 32 where the flow path resistance is high to a location where the flow path resistance is low. Owing to this feature, at an outlet portion where the gas flows out from the filter 32, regardless of the aforementioned flow velocity of the gas at the inlet portion, the flow velocity of the gas becomes substantially constant. Due to the flow path resistance of the filter 32 with respect to the gas, in comparison with the pressure of the gas before having passed through the filter 32, the pressure of the gas after having passed through the filter 32 is lower. However, while passing through the filter 32, because the gas diffuses (spreads out) in the interior of the filter 32, the flow velocity of the gas is suppressed to a speed that is dependent on the external shape of the filter 32. At the aforementioned outlet portion, because the gas flows in from the filter 32 (having an outer diameter of 1 mm) to the supply tube 22 (having an inner diameter of 3 mm), the flow velocity of the gas is further reduced.

On the other hand, in the case that the orifice 30 causes the flow path resistance of the supply pathway to increase, then as shown in FIG. 11B, the flow velocity of the gas after having passed through the orifice 30 remains in a high state. The reason why the flow velocity of the gas after having passed through the orifice 30 is maintained in such a state is as follows.

At an inlet portion where the gas flows into the orifice 30, since the gas flows into the hole of the orifice 30 (having an inner diameter of 0.2 mm) from the supply tube 22 (having an inner diameter of 3 mm), the flow velocity of the gas becomes higher. Due to the flow path resistance of the orifice 30 with respect to the gas, in comparison with the pressure of the gas before having passed through the orifice 30, the pressure of the gas after having passed through the orifice 30 is lower. The axial length of the hole of the orifice 30 is 0.2 mm, and the flow velocity of the gas significantly increases while passing through the hole of the orifice 30. On the other hand, at the outlet portion where the gas flows out from the orifice 30, because the gas flows into the supply tube 22 (having an inner diameter of 3 mm) from the hole of the orifice 30 (having an inner diameter of 0.2 mm), the flow velocity of the gas decreases. However, while the gas is passing through the orifice 30, since the flow velocity of the gas is sufficiently increased, the flow velocity of the gas can be maintained in a high state even inside the supply tube 22.

Based on the results of these simulations, compared to a case in which the filter 32 causes the flow path resistance of the supply pathway to increase, in the case of the orifice 30 causing the flow path resistance of the supply pathway to increase, it was shown that the flow velocity of the gas that flows into the accommodating section 20 is higher.

Figure 12A:
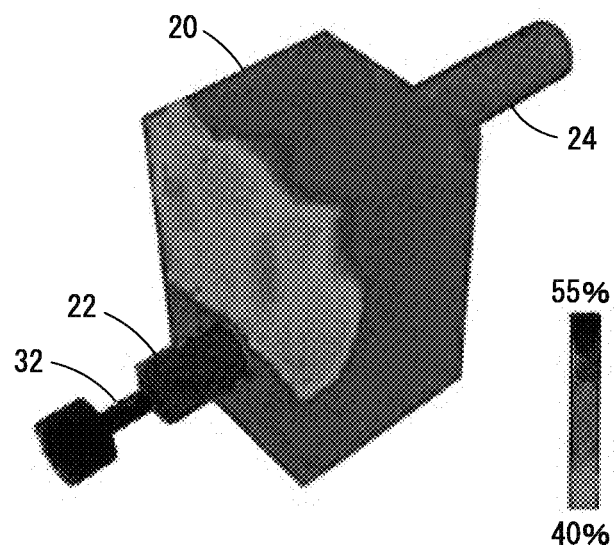
FIGS. 12A and 12B are diagrams showing simulation results.
Figure 12B:
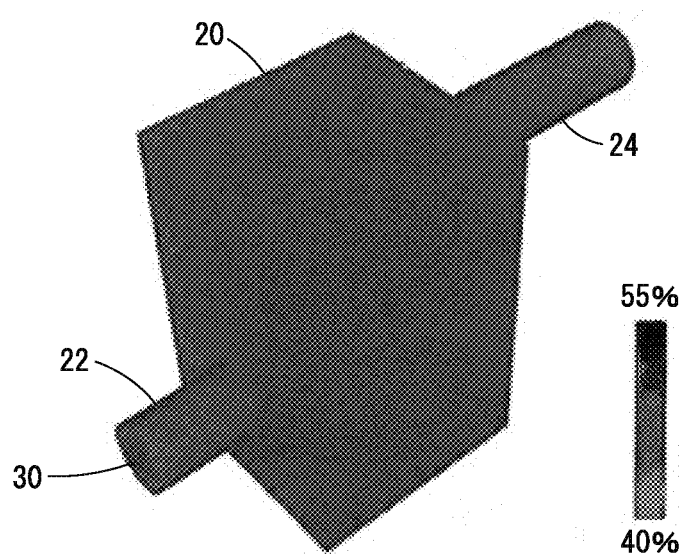

Using a computer, the present inventors have carried out simulations concerning the distribution of the humidity of the gas inside the accommodating section 20. FIGS. 12A and 12B are diagrams showing simulation results. FIG. 12A shows a simulation result in the case that the filter 32 causes the flow path resistance of the supply pathway to increase. FIG. 12B shows a simulation result in the case that the orifice 30 causes the flow path resistance of the supply pathway to increase.

In these simulations, the outer diameter of the filter 32 was set to 1 mm. In these simulations, the length of the filter 32 was set to 4 mm. In these simulations, the diameter of the hole of the orifice 30 was set to 0.2 mm. In these simulations, the length of the hole of the orifice 30 was set to 0.2 mm. In these simulations, the humidity of the gas that flows into the accommodating section 20 was set to 50%. In these simulations, the flow rate of the gas that flows into the accommodating section 20 was set to 1 L/min.

In the case that the filter 32 causes the flow path resistance of the supply pathway to increase, then as shown in FIG. 12A, the distribution of the humidity of the gas in the accommodating section 20 is not uniform. On the other hand, in the case that the orifice 30 causes the flow path resistance of the supply pathway to increase, then as shown in FIG. 12B, the distribution of the humidity of the gas in the accommodating section 20 becomes substantially uniform.

As shown in the simulation results of FIGS. 11A and 11B, compared to a case in which the filter 32 causes the flow path resistance of the supply pathway to increase, in the case of the orifice 30 causing the flow path resistance of the supply pathway to increase, the flow velocity of the gas that flows into the accommodating section 20 is higher. As the flow velocity of the gas that flows into the accommodating section 20 becomes higher, the gas is diffused or spread out over a wider range when the gas collides against the side surface of the accommodating section 20.

According to the simulation results of FIGS. 12A and 12B, compared to a case in which the filter 32 causes the flow path resistance of the supply pathway to increase, in the case of the orifice 30 causing the flow path resistance of the supply pathway to increase, it was shown that the gas that has flowed into the accommodating section 20 became more diffused inside the accommodating section 20.

The present inventors conducted experiments concerning the response speed in measuring the humidity by the temperature and humidity measurement unit 26, with respect to changes in the humidity of the target gas to be measured. In such experiments, by the temperature and humidity measurement unit 26, the present inventors measured the humidity of the gas after having passed through the orifice 30, and the humidity of the gas after having passed through the filter 32. In such experiments, the diameter of the hole of the orifice 30 was set to 0.25 mm. In such experiments, the outer diameter of the filter 32 was set to 1.0 mm.

In a first experiment (hereinafter referred to as Experiment 1), prior to starting of the experiment, the accommodating section 20 was filled with a gas having a humidity of 5%. The gas having a humidity of 5% was supplied to the accommodating section 20 over a period of 5 seconds after having started the experiment. After passage of 5 seconds from having started the experiment, supply of a gas having a humidity of 45% into the accommodating section 20 was initiated. In a second experiment (hereinafter referred to as Experiment 2), prior to starting of the experiment, the accommodating section 20 was filled with a gas having a humidity of 45%. The gas having a humidity of 45% was supplied to the accommodating section 20 over a period of 5 seconds after having started the experiment. After passage of 5 seconds from having started the experiment, supply of a gas having a humidity of 5% into the accommodating section 20 was initiated.

Figure 13A:
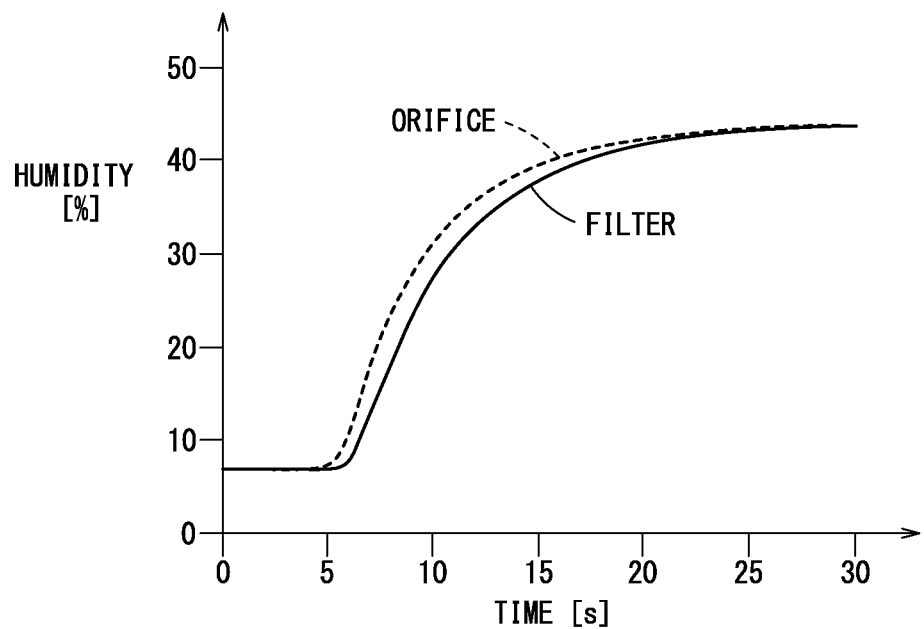
FIGS. 13A and 13B are graphs showing experimental results.
Figure 13B:
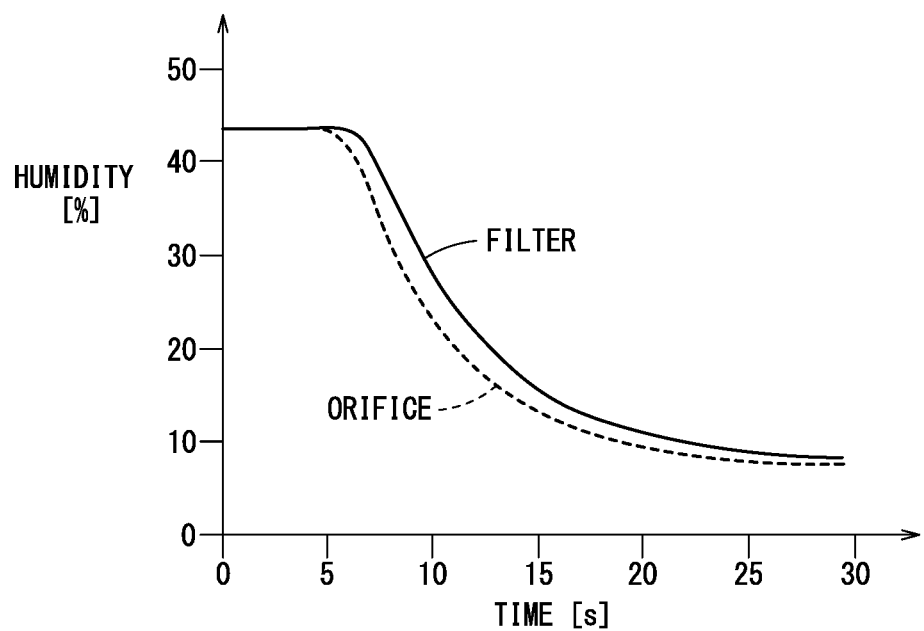

FIGS. 13A and 13B show experimental results. FIG. 13A shows the experimental results of Experiment 1 in which the humidity of the gas supplied to the accommodating section 20 was made to change so as to become higher from 5% to 45%. FIG. 13B shows the experimental results of Experiment 2 in which the humidity of the gas supplied to the accommodating section 20 was made to change so as to become lower from 45% to 5%. In Experiment 1, the measured humidity of the gas after having passed through the orifice 30 rises more rapidly than the measured humidity of the gas after having passed through the filter 32. In Experiment 2, the measured humidity of the gas after having passed through the orifice 30 decreases more rapidly than the measured humidity of the gas after having passed through the filter 32.

From these experimental results, compared to the case in which the filter 32 causes the flow path resistance of the supply pathway to increase, in the case of the orifice 30 causing the flow path resistance of the supply pathway to increase, it was shown that the response speed in measuring the humidity of the target gas to be measured by the temperature and humidity measurement unit 26 is improved, with respect to changes in the humidity of the target gas to be measured.

Actions and Effects

In the humidity measuring device 10 according to the present embodiment, the display unit 14 is fixed to the casing 12. The display unit 14 includes the display device 54. The display device 54 displays the humidity of the gas, the temperature of the gas, and the dew point temperature of the gas. Consequently, the user is capable of confirming the humidity of the gas, the temperature of the gas, and the dew point temperature of the gas, at the location where the humidity measuring device 10 is installed.

In the humidity measuring device 10 according to the present embodiment, the first output unit 44 outputs to the external device 46 the comparison result between the set humidity and the humidity (the measured humidity) of the gas measured by the temperature and humidity measurement unit 26. Consequently, the humidity measuring device 10 according to the present embodiment is capable of outputting to the external device 46 the comparison result between the set humidity and the measured humidity.

In the humidity measuring device 10 according to the present embodiment, the first output unit 44 outputs to the external device 46 the comparison result between the set dew point temperature and the dew point temperature (the calculated dew point temperature) of the gas calculated by the dew point temperature calculation unit 40. Consequently, the humidity measuring device 10 according to the present embodiment is capable of outputting to the external device 46 the comparison result between the set dew point temperature and the calculated dew point temperature.

In the humidity measuring device 10 according to the present embodiment, the second output unit 48 outputs to the external device 50 the humidity (the measured humidity) of the gas measured by the temperature and humidity measurement unit 26. Consequently, the humidity measuring device 10 according to the present embodiment is capable of outputting the measured humidity to the external device 50.

In the humidity measuring device 10 according to the present embodiment, the second output unit 48 outputs to the external device 50 the dew point temperature (the calculated dew point temperature) of the gas calculated by the dew point temperature calculation unit 40. Consequently, the humidity measuring device 10 according to the present embodiment is capable of outputting the calculated dew point temperature to the external device 50.

In the humidity measuring device 10 according to the present embodiment, the direction in which the gas flows from the supply tube 22 into the accommodating section 20, and the direction in which the gas flows out from the accommodating section 20 into the discharge tube 24 are positioned mutually on different straight lines. In accordance with this feature, the temperature and humidity measurement unit 26 according to the present embodiment is capable of improving the accuracy in measuring the humidity of the gas.

In the humidity measuring device 10 according to the present embodiment, the connecting tube 28 includes the orifice 30. The cross-sectional area of the hole of the orifice 30 is smaller than the cross-sectional area of the discharge tube 24. Consequently, the flow path resistance of the gas supply pathway becomes larger than the flow path resistance of the gas discharge pathway. Therefore, the pressure of the gas inside the accommodating section 20 can be set to the atmospheric pressure. The dew point temperature calculation unit 40 can calculate the dew point temperature under atmospheric pressure of the gas, based on the temperature of the gas and the humidity of the gas measured by the temperature and humidity measurement unit 26.

In the humidity measuring device 10 according to the present embodiment, the filter 32 is mounted in the connecting tube 28. Further, the orifice 30 is arranged in closer proximity to the side of the accommodating section 20 than the filter 32. Owing to these features, it is possible to prevent foreign material from clogging the hole of the orifice 30 of the connection tube 28.

In the humidity measuring device 10 according to the present embodiment, the filter 32 is made of metal. Consequently, it is possible to prevent moisture in the gas from being absorbed by the filter 32. Therefore, the humidity measuring device 10 according to the present embodiment is capable of improving the accuracy in measuring the humidity of the gas.

In the humidity measuring device 10 according to the present embodiment, the user is capable of removing the connecting portion 18 from the main body portion 16 in a state in which the filter 32 is mounted in the connecting portion 18. Thus, the user is capable of easily replacing the filter 32 of the humidity measuring device 10.

Second Embodiment

Figure 14:
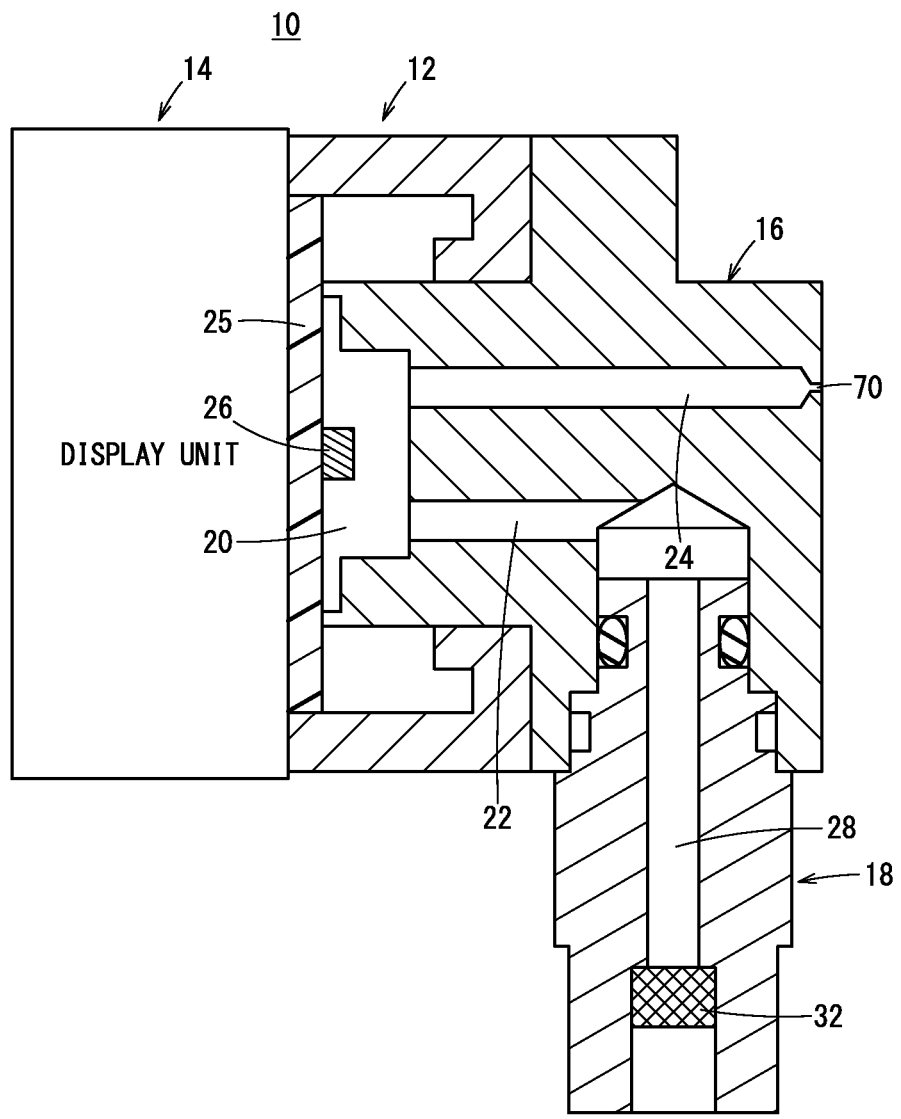
FIG. 14 is a view showing the humidity measuring device.

FIG. 14 shows the humidity measuring device 10. In FIG. 14, a cross-sectional view of a casing 12 is shown. In FIG. 14, a schematic diagram of the display unit 14 is shown.

In the humidity measuring device 10 according to the first embodiment, the connecting tube 28 that is formed in the interior of the connecting portion 18 includes the orifice 30 (see FIG. 1). In contrast thereto, in the humidity measuring device 10 according to the present embodiment, the connecting tube 28 that is formed in the interior of the connecting portion 18 does not include the orifice (see FIG. 14). In the humidity measuring device 10 according to the present embodiment, the discharge tube 24 that is formed in the interior of the main body portion 16 of the casing 12 includes an orifice 70. In the orifice 70, the cross-sectional area of a minimum diameter portion of the hole of the orifice 70 is smaller than the cross-sectional area of the supply tube 22. In the orifice 70, the cross-sectional area of the minimum diameter portion of the hole of the orifice 70 is also smaller than the cross-sectional area of the connecting tube 28. Other constituent features of the humidity measuring device 10 according to the present embodiment are the same as the constituent features of the humidity measuring device 10 according to the first embodiment.

Since the connecting tube 28 does not include an orifice, and the discharge tube 24 includes the orifice 70, the pressure of the gas inside the accommodating section 20 becomes substantially the same as the pressure of the compressed gas inside the tube 36, or alternatively, the pressure of the compressed gas that is discharged by the dehumidifying device 38. The temperature and humidity measurement unit 26 measures the temperature under the pressure of the gas. The temperature and humidity measurement unit 26 measures the humidity under the pressure of the gas. The dew point temperature calculation unit 40 of the display unit 14 calculates the dew point temperature under the pressure of the gas, based on the temperature under the pressure of the gas measured by the temperature and humidity measurement unit 26, and the humidity under the pressure of the gas measured by the temperature and humidity measurement unit 26.

Actions and Effects

In the humidity measuring device 10 according to the present embodiment, the discharge tube 24 includes the orifice 70. The cross-sectional area of the hole of the orifice 70 is smaller than the cross-sectional area of the supply tube 22. In the orifice 70, the cross-sectional area of the hole of the orifice 70 is smaller than the cross-sectional area of the connecting tube 28. Since the connecting tube 28 does not include an orifice, and the discharge tube 24 includes the orifice 70, the pressure of the gas inside the accommodating section 20 becomes substantially the same as the pressure of the compressed gas inside the tube 36, or alternatively, the pressure of the compressed gas that is discharged by the dehumidifying device 38. The temperature and humidity measurement unit 26 is capable of measuring the temperature under the pressure of the gas. The temperature and humidity measurement unit 26 is capable of measuring the humidity under the pressure of the gas. The dew point temperature calculation unit 40 is capable of calculating the dew point temperature under the pressure of the gas, based on the temperature under the pressure of the gas measured by the temperature and humidity measurement unit 26, and the humidity under the pressure of the gas measured by the temperature and humidity measurement unit 26.

Third Embodiment

Figure 15:
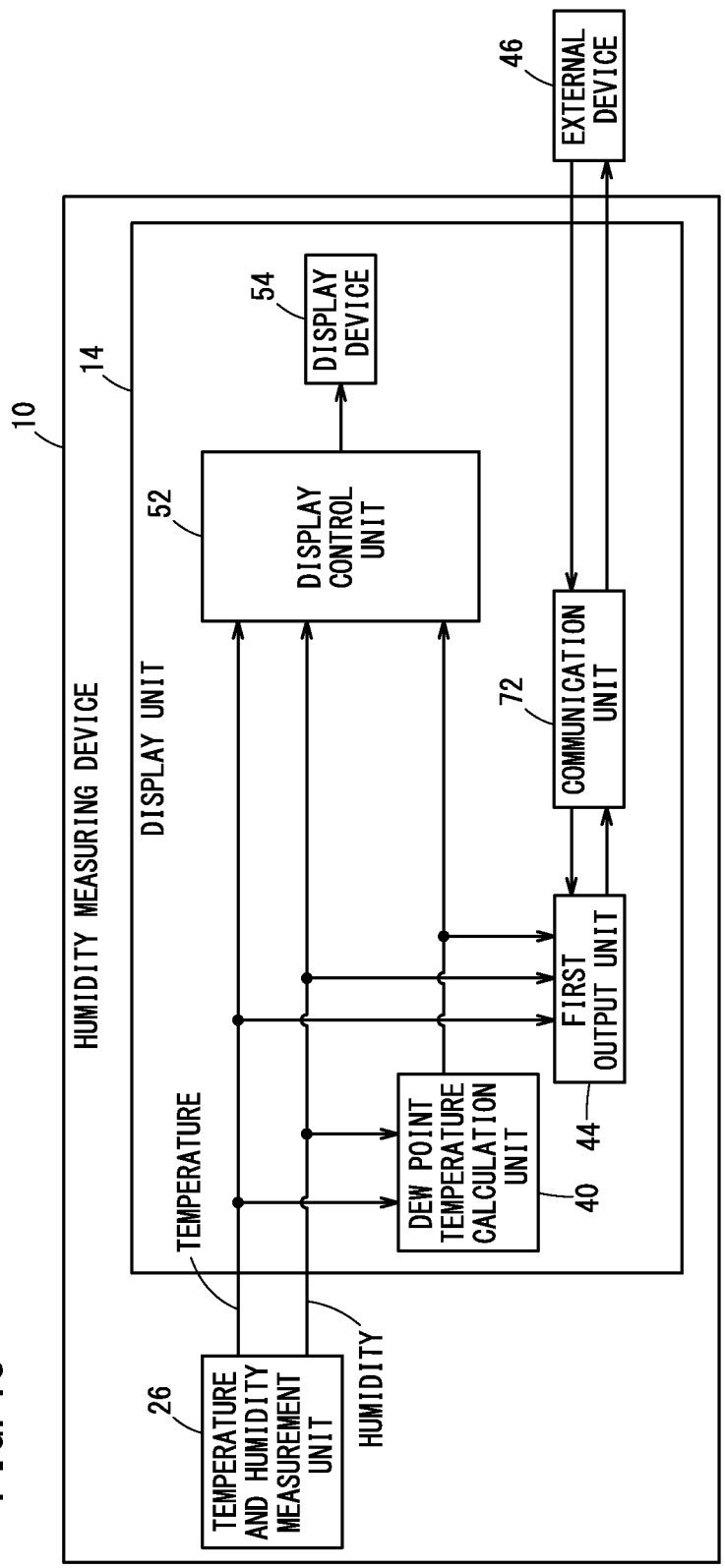
FIG. 15 is a control block diagram of the humidity measuring device.

FIG. 15 is a control block diagram of the humidity measuring device 10. With reference to the control block diagram of FIG. 15, a description will be given concerning the configuration of the display unit 14.

The display unit 14 of the humidity measuring device 10 according to the present embodiment includes the dew point temperature calculation unit 40, the first output unit 44, the display control unit 52, the display device 54, and a communication unit 72. The dew point temperature calculation unit 40, the display control unit 52, and the display device 54 are the same as the dew point temperature calculation unit 40, the display control unit 52, and the display device 54 of the display unit 14 of the humidity measuring device 10 according to the first embodiment.

The communication unit 72 carries out communications with the external device 46. The communication unit 72 receives the set temperature, the set humidity, and the set dew point temperature from the external device 46. The communication unit 72 outputs to the first output unit 44 the set temperature, the set humidity, and the set dew point temperature received by the communication unit 72. The set temperature, the set humidity, and the set dew point temperature may be values set by the user of the external device 46. The set temperature, the set humidity, and the set dew point temperature may also be values set by a manufacturer of the external device 46 at a time of shipment of the humidity measuring device 10.

The first output unit 44 outputs to the communication unit 72 a comparison result between the set temperature and the measured temperature. The first output unit 44 outputs to the communication unit 72 a comparison result between the set humidity and the measured humidity. The first output unit 44 outputs to the communication unit 72 the comparison result between the set dew point temperature and the calculated dew point temperature.

The communication unit 72 transmits to the external device 46 the comparison result between the set temperature and the measured temperature. The communication unit 72 transmits to the external device 46 the comparison result between the set humidity and the measured humidity. The communication unit 72 transmits to the external device 46 the comparison result between the set dew point temperature and the calculated dew point temperature.

Actions and Effects

In the humidity measuring device 10 according to the present embodiment, the display unit 14 includes the communication unit 72. The communication unit 72 carries out communications with the external device 46. The communication unit 72 is capable of receiving the respective set values which are set on the side of the external device 46. In accordance with these features, in the humidity measuring device 10 according to the present embodiment, the first output unit 44 is capable of comparing the respective set values that are set in the external device 46 with each of the measured temperature, the measured humidity, and the calculated dew point temperature. In the humidity measuring device 10 according to the present embodiment, the communication unit 72 is capable of transmitting to the external device 46 the comparison results compared by the first output unit 44.

Fourth Embodiment

Figure 16:
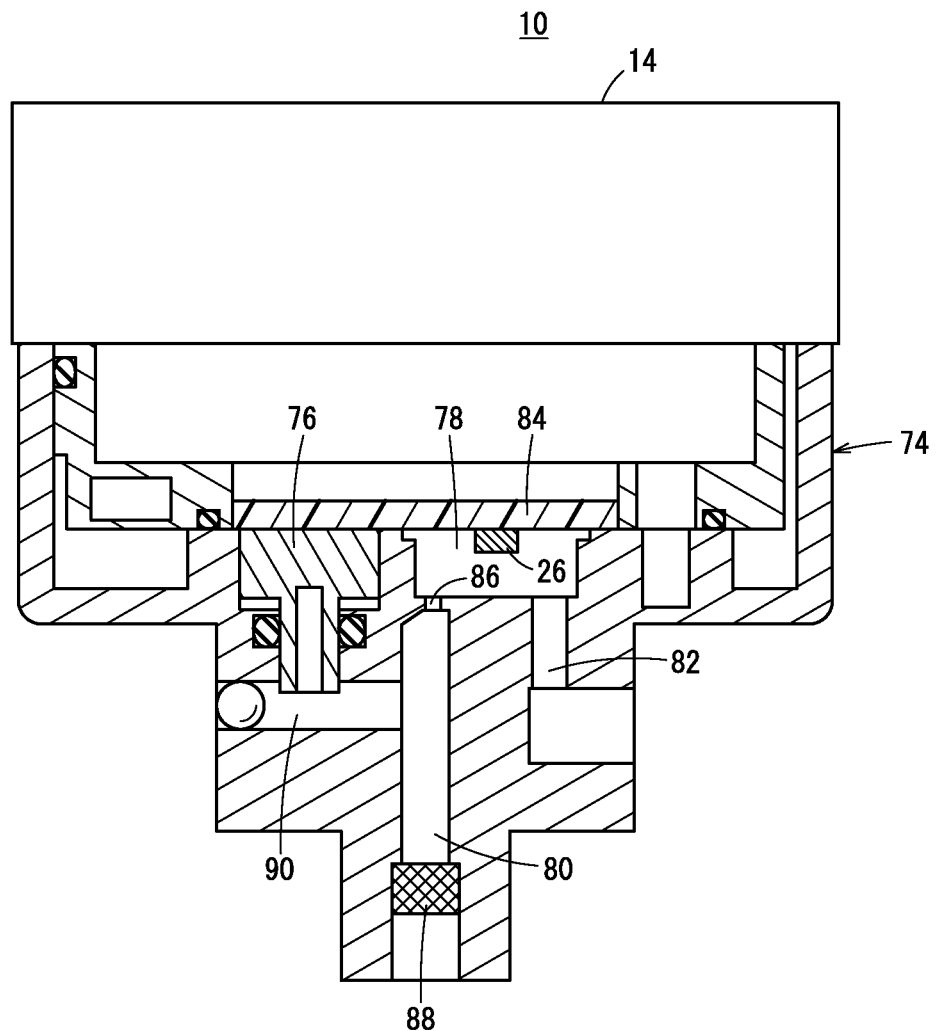
FIG. 16 is a view showing the humidity measuring device.

FIG. 16 shows the humidity measuring device 10. The humidity measuring device 10 includes a casing 74 and the display unit 14. In FIG. 16, a cross-sectional view of the casing 74 is shown. In FIG. 16, a schematic diagram of the display unit 14 is shown.

The casing 74 includes an accommodating section 78 in the interior of the casing 74. The casing 74 includes a supply tube 80 in the interior of the casing 74. The casing 74 includes a discharge tube 82 in the interior of the casing 74. The supply tube 80 is connected to the accommodating section 78. The discharge tube 82 is connected to the accommodating section 78. The gas, which is a target gas to be measured by the humidity measuring device 10, is supplied from the supply tube 80 to the accommodating section 78. The gas that is supplied into the accommodating section 78 is discharged from the discharge tube 82 into the atmosphere. An opening of the discharge tube 82 in the accommodating section 78 is arranged at a position that is offset, with respect to the opening of the supply tube 80 in the accommodating section 78, in a radial direction of the opening of the supply tube 80.

The humidity measuring device 10 includes an electronic circuit board 84. The electronic circuit board 84 is arranged between the casing 74 and the display unit 14. The temperature and humidity measurement unit 26 is mounted on the electronic circuit board 84. The temperature and humidity measurement unit 26 is accommodated in the accommodating section 78.

The supply tube 80 includes an orifice 86. A filter 88 is mounted in the supply tube 80. The filter 88 is made of metal. The orifice 86 is arranged at a position in closer proximity to the accommodating section 78 than the position where the filter 88 is mounted. In the orifice 86, the cross-sectional area of a minimum diameter portion of the hole of the orifice 86 is smaller than the cross-sectional area of the discharge tube 82. Therefore, a flow path resistance of a pathway (hereinafter, referred to as a discharge pathway) through which the gas from the accommodating section 78 is discharged is smaller than a flow path resistance of a pathway (hereinafter, referred to as a supply pathway) through which the gas is supplied to the accommodating section 78. Consequently, the pressure of the gas inside the accommodating section 78 becomes the atmospheric pressure. The temperature and humidity measurement unit 26 measures the temperature of the gas inside the accommodating section 78. The temperature and humidity measurement unit 26 measures the humidity of the gas inside the accommodating section 78. The temperature and humidity measurement unit 26 outputs to the display unit 14 the temperature and humidity of the gas that were measured.

The casing 74 includes a branching tube 90 in the interior of the casing 74. The branching tube 90 is connected to the supply tube 80. A connected position of the branching tube 90 in the supply tube 80 is between the orifice 86 of the supply tube 80 and the filter 88. A pressure measurement unit 76 is mounted on the electronic circuit board 84. The branching tube 90 supplies the gas prior to passing through the orifice 86 to the pressure measurement unit 76. The pressure measurement unit 76 measures the pressure of the supplied gas. In the case that the humidity measuring device 10 is installed in the tube 36, the pressure of the gas supplied to the pressure measurement unit 76 is substantially the same as the pressure of the compressed gas that flows through the tube 36. In the case that the humidity measuring device 10 is installed in the dehumidifying device 38, the pressure of the gas supplied to the pressure measurement unit 76 is substantially the same as the pressure of the compressed gas discharged from the dehumidifying device 38. Consequently, the pressure measurement unit 76 is capable of measuring the pressure of the gas at the measurement location.

Figure 17:
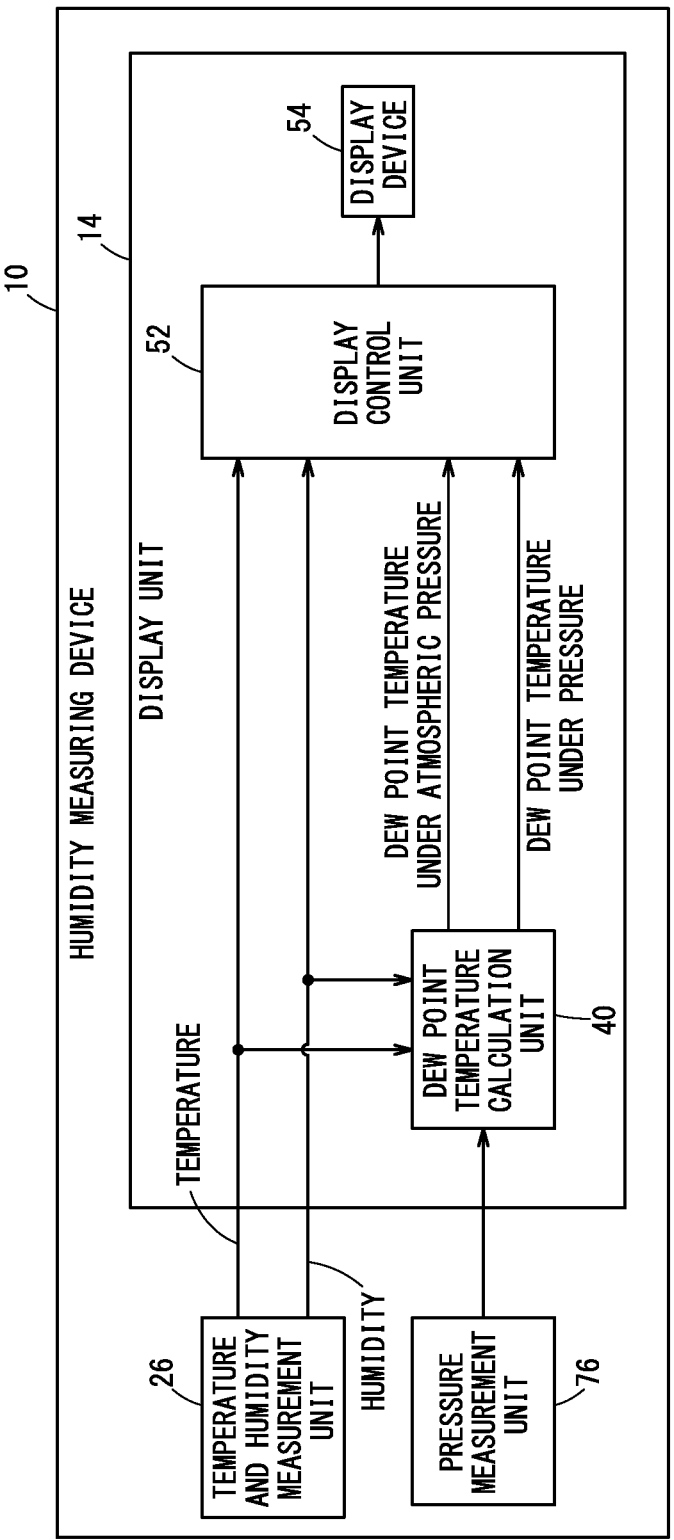
FIG. 17 is a control block diagram of the humidity measuring device.

FIG. 17 is a control block diagram of the humidity measuring device 10. With reference to the control block diagram of FIG. 17, a description will be given concerning the configuration of the display unit 14.

The display unit 14 of the humidity measuring device 10 according to the present embodiment includes the dew point temperature calculation unit 40, the display control unit 52, and the display device 54. The display control unit 52 and the display device 54 of the display unit 14 of the humidity measuring device 10 according to the present embodiment are the same as the display control unit 52 and the display device 54 of the display unit 14 of the humidity measuring device 10 according to the first embodiment.

The temperature under atmospheric pressure of the gas measured by the temperature and humidity measurement unit 26 is input to the dew point temperature calculation unit 40. The humidity under atmospheric pressure of the gas measured by the temperature and humidity measurement unit 26 is input to the dew point temperature calculation unit 40. The pressure of the gas measured by the pressure measurement unit 76 is input to the dew point temperature calculation unit 40. In the case that the humidity measuring device 10 is installed in the tube 36, the pressure measurement unit 76 measures the pressure of the compressed gas that flows through the interior of the tube 36. In the case that the humidity measuring device 10 is installed in the dehumidifying device 38, the pressure measurement unit 76 measures the pressure of the compressed gas discharged from the dehumidifying device 38. The dew point temperature calculation unit 40 calculates the dew point temperature under atmospheric pressure of the gas, based on the temperature under atmospheric pressure of the gas measured by the temperature and humidity measurement unit 26, and the humidity under atmospheric pressure of the gas measured by the temperature and humidity measurement unit 26. The dew point temperature calculation unit 40 corrects the dew point temperature under atmospheric pressure of the gas, which was calculated by the dew point temperature calculation unit 40, in accordance with the pressure of the gas measured by the pressure measurement unit 76, and thereby calculates the dew point temperature under the pressure of the gas.

Actions and Effects

Even if an absolute humidity of the gas (an amount of moisture contained in the gas) is the same, as the pressure of the gas becomes higher, the higher the dew point temperature becomes. Therefore, as the pressure of the gas in contact with the temperature and humidity measurement unit 26 is higher, it becomes easier for water droplets to become adhered to the temperature and humidity measurement unit 26. In the case that water droplets adhere in this manner to the temperature and humidity measurement unit 26, a concern arises in that the humidity measured by the temperature and humidity measurement unit 26 may become an abnormal value.

The humidity measuring device 10 according to the present embodiment includes the pressure measurement unit 76 that measures the pressure of the gas at the measurement position where the humidity measuring device 10 measures the humidity and the like of the gas. The dew point temperature calculation unit 40 calculates the dew point temperature under atmospheric pressure of the gas, which is calculated based on the temperature under atmospheric pressure of the gas measured by the temperature and humidity measurement unit 26, and the humidity under atmospheric pressure of the gas measured by the temperature and humidity measurement unit 26. The dew point temperature calculation unit 40 corrects the dew point temperature under atmospheric pressure of the gas, which was calculated by the dew point temperature calculation unit 40, in accordance with the pressure of the gas measured by the pressure measurement unit 76, and thereby calculates the dew point temperature under the pressure of the gas. Consequently, since the temperature and humidity measurement unit 26 does not come into contact with the high pressure gas, the adherence of water droplets to the temperature and humidity measurement unit 26 is suppressed.

Fifth Embodiment

Figure 18:
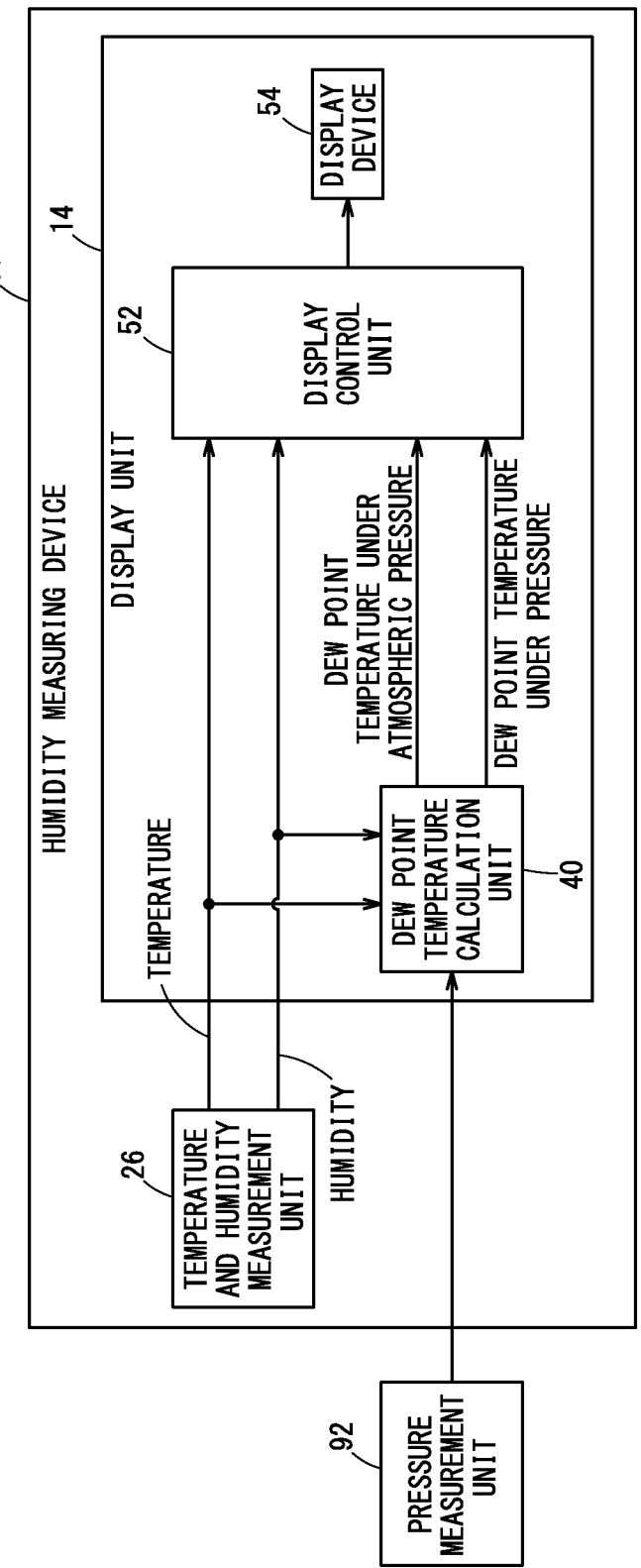
FIG. 18 is a control block diagram of the humidity measuring device.

FIG. 18 is a control block diagram of the humidity measuring device 10. With reference to the control block diagram of FIG. 18, a description will be given concerning the configuration of the display unit 14.

The display unit 14 of the humidity measuring device 10 according to the present embodiment includes the dew point temperature calculation unit 40, the display control unit 52, and the display device 54. The display control unit 52 and the display device 54 of the display unit 14 of the humidity measuring device 10 according to the present embodiment are the same as the display control unit 52 and the display device 54 of the display unit 14 of the humidity measuring device 10 according to the first embodiment.

The temperature under atmospheric pressure of the gas measured by the temperature and humidity measurement unit 26 is input to the dew point temperature calculation unit 40. The humidity under atmospheric pressure of the gas measured by the temperature and humidity measurement unit 26 is input to the dew point temperature calculation unit 40. The pressure of the gas, which is measured by a pressure measurement unit 92, is input to the dew point temperature calculation unit 40.

The pressure measurement unit 92 is disposed externally of the humidity measuring device 10. In the case that the humidity measuring device 10 is installed in the tube 36, the pressure measurement unit 92 measures the pressure of the compressed gas that flows through the interior of the tube 36. In the case that the humidity measuring device 10 is installed in the dehumidifying device 38, the pressure measurement unit 92 measures the pressure of the compressed gas discharged from the dehumidifying device 38.

The dew point temperature calculation unit 40 calculates the dew point temperature under atmospheric pressure of the gas, based on the temperature under atmospheric pressure of the gas measured by the temperature and humidity measurement unit 26, and the humidity under atmospheric pressure of the gas measured by the temperature and humidity measurement unit 26. The dew point temperature calculation unit 40 corrects the dew point temperature under atmospheric pressure of the gas, which was calculated by the dew point temperature calculation unit 40, in accordance with the pressure of the gas measured by the pressure measurement unit 92, and thereby calculates the dew point temperature under the pressure of the gas.

Actions and Effects

In the humidity measuring device 10 according to the present embodiment, the dew point temperature calculation unit 40 calculates the dew point temperature under atmospheric pressure of the gas, based on the temperature under atmospheric pressure of the gas measured by the temperature and humidity measurement unit 26, and the humidity under atmospheric pressure of the gas measured by the temperature and humidity measurement unit 26. The dew point temperature calculation unit 40 corrects the dew point temperature under atmospheric pressure of the gas, which was calculated by the dew point temperature calculation unit 40, in accordance with the pressure of the gas measured by the pressure measurement unit 92 that is disposed externally of the humidity measuring device 10, and thereby calculates the dew point temperature under the pressure of the gas. Consequently, since the temperature and humidity measurement unit 26 does not come into contact with the high pressure gas, the adherence of water droplets to the temperature and humidity measurement unit 26 is suppressed.

Sixth Embodiment

Figure 19:
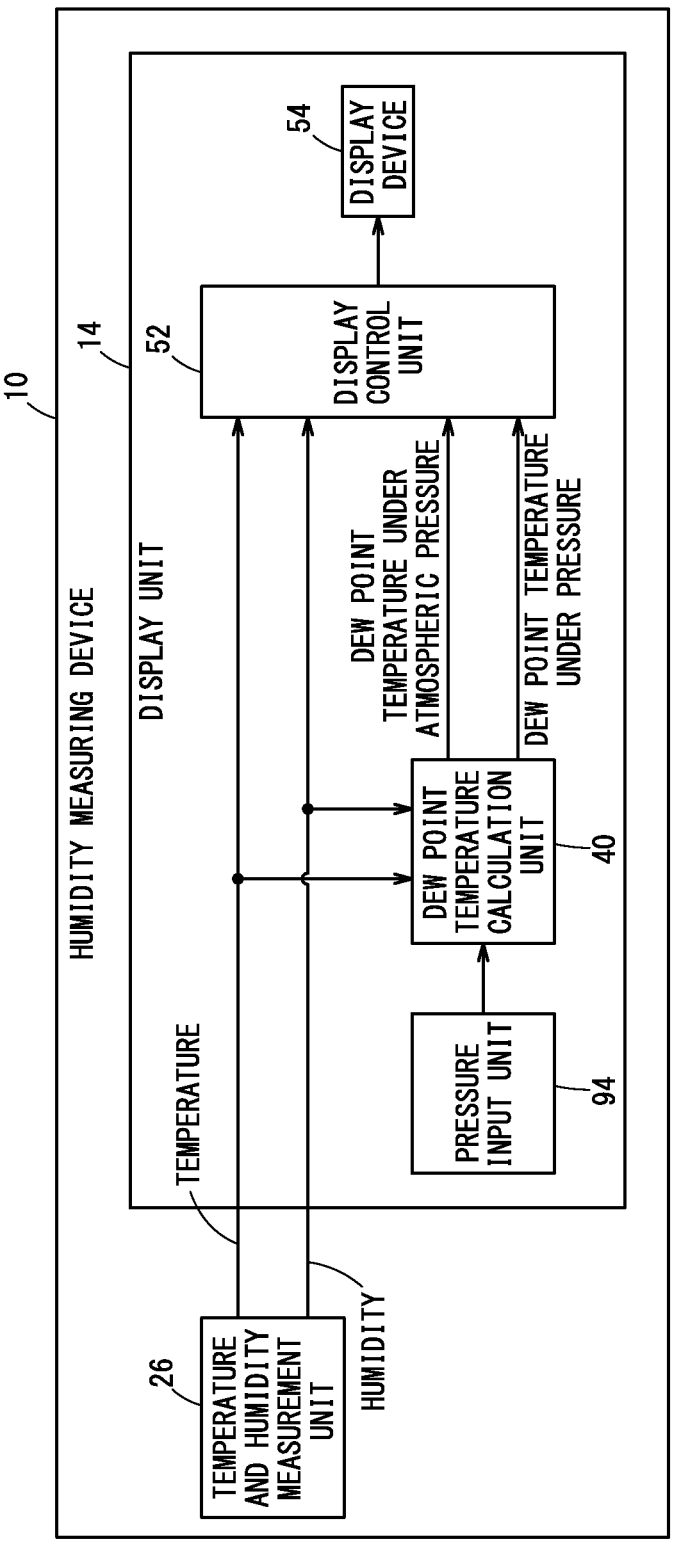
FIG. 19 is a control block diagram of the humidity measuring device.

FIG. 19 is a control block diagram of the humidity measuring device 10. With reference to the control block diagram of FIG. 19, a description will be given concerning the configuration of the display unit 14.

The display unit 14 of the humidity measuring device 10 according to the present embodiment includes the dew point temperature calculation unit 40, the display control unit 52, the display device 54, and a pressure input unit 94. The display control unit 52 and the display device 54 of the display unit 14 of the humidity measuring device 10 according to the present embodiment are the same as the display control unit 52 and the display device 54 of the display unit 14 of the humidity measuring device 10 according to the first embodiment.

The pressure input unit 94 inputs the pressure of the gas to the dew point temperature calculation unit 40. The pressure of the gas that is output to the dew point temperature calculation unit 40 by the pressure input unit 94 may be a value set by the user. The pressure of the gas that is output to the dew point temperature calculation unit 40 by the pressure input unit 94 may be a value set by a manufacturer of the humidity measuring device 10 at a time of shipment of the humidity measuring device 10. In the case that the pressure of the compressed gas that flows through the tube 36 is substantially constant, a pressure that was set beforehand may be input to the dew point temperature calculation unit 40. Similarly, in the case that the pressure of the compressed gas discharged by the dehumidifying device 38 is substantially constant, a pressure that was set beforehand may be input to the dew point temperature calculation unit 40.

The temperature under atmospheric pressure of the gas measured by the temperature and humidity measurement unit 26 is input to the dew point temperature calculation unit 40. The humidity under atmospheric pressure of the gas measured by the temperature and humidity measurement unit 26 is input to the dew point temperature calculation unit 40. The pressure of the gas from the pressure input unit 94 is input to the dew point temperature calculation unit 40.

The dew point temperature calculation unit 40 calculates the dew point temperature under atmospheric pressure of the gas, based on the temperature under atmospheric pressure of the gas measured by the temperature and humidity measurement unit 26, and the humidity under atmospheric pressure of the gas measured by the temperature and humidity measurement unit 26. The dew point temperature calculation unit 40 corrects the dew point temperature under atmospheric pressure of the gas, which was calculated by the dew point temperature calculation unit 40, in accordance with the pressure of the gas input from the pressure input unit 94, and thereby calculates the dew point temperature under the pressure of the gas.

Actions and Effects

In the humidity measuring device 10 according to the present embodiment, the dew point temperature calculation unit 40 calculates the dew point temperature under atmospheric pressure of the gas, based on the temperature under atmospheric pressure of the gas measured by the temperature and humidity measurement unit 26, and the humidity under atmospheric pressure of the gas measured by the temperature and humidity measurement unit 26. The dew point temperature calculation unit 40 corrects the dew point temperature under atmospheric pressure of the gas, which was calculated by the dew point temperature calculation unit 40, in accordance with the pressure of the gas input from the pressure input unit 94, and thereby calculates the dew point temperature under the pressure of the gas. Consequently, since the temperature and humidity measurement unit 26 does not come into contact with the high pressure gas, the adherence of water droplets to the temperature and humidity measurement unit 26 is suppressed.

Seventh Embodiment

Figure 20:
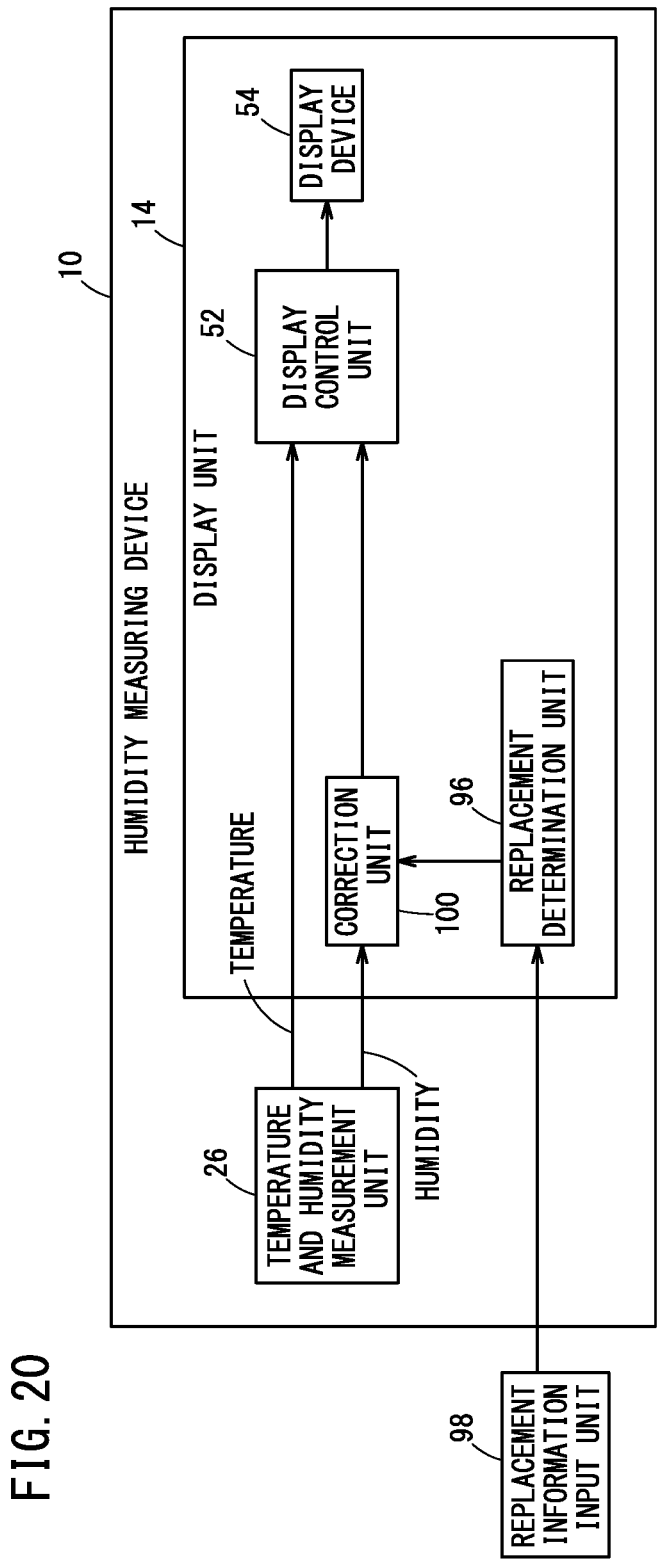
FIG. 20 is a control block diagram of the humidity measuring device.

FIG. 20 is a control block diagram of the humidity measuring device 10. With reference to the control block diagram of FIG. 20, a description will be given concerning the configuration of the display unit 14.

The display unit 14 of the humidity measuring device 10 according to the present embodiment includes the display control unit 52, the display device 54, a replacement determination unit 96, and a correction unit 100. The display control unit 52 and the display device 54 of the display unit 14 of the humidity measuring device 10 according to the present embodiment are the same as the display control unit 52 and the display device 54 of the display unit 14 of the humidity measuring device 10 according to the first embodiment.

When the dehumidifying device 38 is replaced, information indicating that the dehumidifying device 38 has been replaced is input from a replacement information input unit 98 to the replacement determination unit 96. The replacement information input unit 98 is disposed externally of the humidity measuring device 10. The dehumidifying device 38 may include the replacement information input unit 98. In the case that information from the replacement information input unit 98 indicating that the dehumidifying device 38 has been replaced is input to the replacement determination unit 96, the replacement determination unit 96 determines that the dehumidifying device 38 has been replaced. In the case that information from the replacement information input unit 98 indicating that the dehumidifying device 38 has been replaced is not input to the replacement determination unit 96, the replacement determination unit 96 determines that the dehumidifying device 38 has not been replaced.

The humidity of the gas measured by the temperature and humidity measurement unit 26 is input to the correction unit 100. The determination result determined by the replacement determination unit 96 is also input to the correction unit 100. The correction unit 100, in accordance with the determination result that is input thereto, corrects the humidity measured by the temperature and humidity measurement unit 26.

Figure 21:
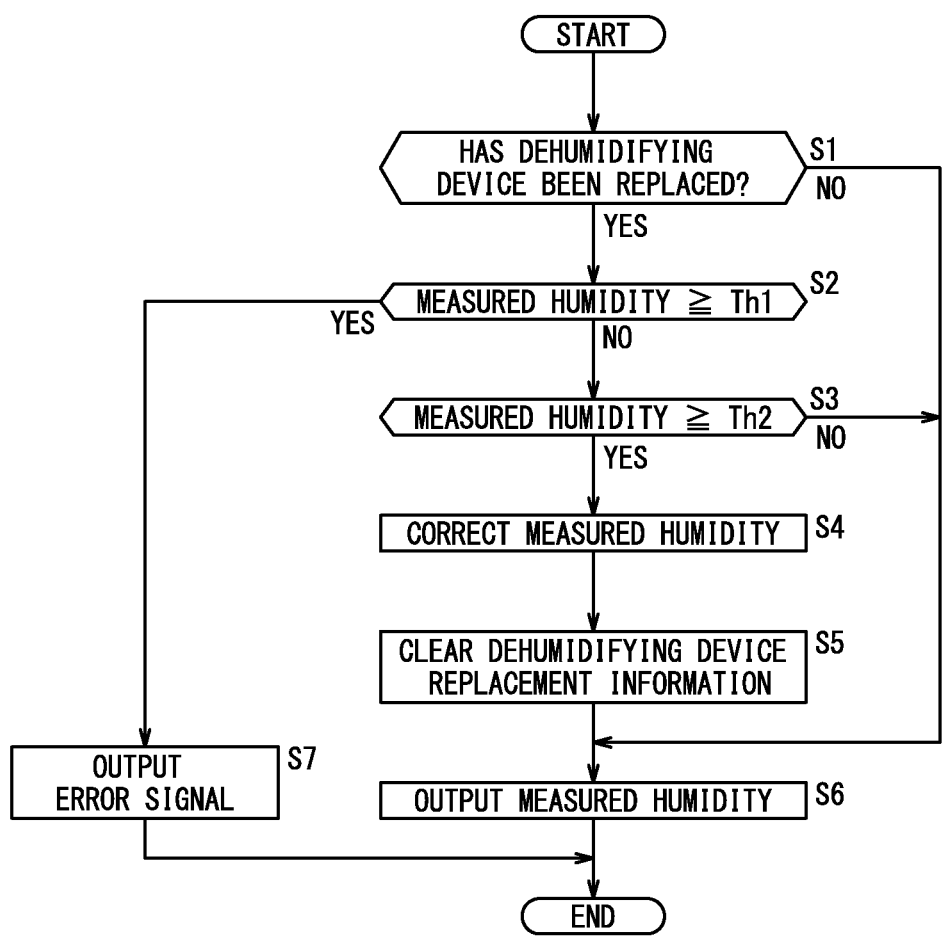
FIG. 21 is a flowchart showing a process flow of a correction process.

FIG. 21 is a flowchart showing a process flow of a correction process executed in the replacement determination unit 96 and the correction unit 100. The correction process is repeatedly executed at a predetermined cycle.

In step S1, the replacement determination unit 96 determines whether or not the dehumidifying device 38 has been replaced, between a time from when the process of step S1 has been executed in a previous cycle until a time when the process of step S1 is executed in the current cycle. When information from the replacement information input unit 98 indicating that the dehumidifying device 38 has been replaced is input thereto, the replacement determination unit 96 determines that the dehumidifying device 38 has been replaced. In the case that the replacement determination unit 96 has determined that the dehumidifying device 38 has been replaced (step S1: YES), the correction process proceeds to step S2. In the case that the replacement determination unit 96 has determined that the dehumidifying device 38 has not been replaced (step S1: NO), the correction process proceeds to step S6.

In step S2, the correction unit 100 determines whether or not the humidity (measured humidity) of the gas measured by the temperature and humidity measurement unit 26 is greater than or equal to a first threshold value Th1. In the case that the measured humidity is greater than or equal to the first threshold value Th1 (step S2: YES), the correction process proceeds to step S7. In the case that the measured humidity is less than the first threshold value Th1 (step S2: NO), the correction process proceeds to step S3.

In step S3, the correction unit 100 determines whether or not the measured humidity is greater than or equal to a second threshold value Th2. In the case that the measured humidity is greater than or equal to the second threshold value Th2 (step S3: YES), the correction process proceeds to step S4. In the case that the measured humidity is less than the second threshold value Th2 (step S3: NO), the correction process proceeds to step S6. The second threshold value Th2 is a smaller value than the first threshold value Th1.

In step S4, the correction unit 100 corrects the measured humidity and thereby obtains a new measured humidity. Thereafter, the correction process proceeds to step S5. Hereinafter, the new measured humidity obtained by the correction unit 100 may be referred to as a corrected humidity.

In step S5, the replacement determination unit 96 clears the information (dehumidifying device replacement information), which was input from the replacement information input unit 98, indicating that the dehumidifying device 38 has been replaced. Thereafter, the correction process proceeds to step S6.

In step S6, the correction unit 100 outputs the measured humidity to the display control unit 52. Thereafter, the correction process comes to an end.

In step S7, after it has been determined in step S2 that the measured humidity is greater than or equal to the first threshold value Th1 (step S2: YES), the correction unit 100 outputs an error signal to the display control unit 52. Thereafter, the correction process comes to an end. In the case that the error signal is input to the display control unit 52, the display control unit 52 controls the display device 54 to thereby cause there to be displayed on the display device 54 a display prompting the user to replace the temperature and humidity measurement unit 26.

Actions and Effect

The humidity sensing element of the temperature and humidity measurement unit 26 includes a humidity sensitive membrane. A capacitance of the humidity sensitive membrane changes in accordance with an amount of moisture contained within the humidity sensitive membrane. The humidity sensing element measures the humidity of the gas based on the capacitance of the humidity sensitive membrane.

Accompanying deterioration of the humidity sensitive membrane, the capacitance of the humidity sensitive membrane corresponding to the humidity of the gas changes. The reason for this is due to permeation of water into the moisture sensitive membrane, dirt on the humidity sensitive membrane, or the like. Therefore, accompanying the deterioration of the humidity sensitive membrane, the accuracy of the measured humidity as measured by the temperature and humidity measurement unit 26 decreases.

Immediately after the dehumidifying device 38 has been replaced, it is considered that the humidity of the gas after being dehumidified by the dehumidifying device 38 should be adjusted to a predetermined humidity in accordance with the dehumidifying ability of the dehumidifying device 38. In the case that the measured humidity measured by the temperature and humidity measurement unit 26 is higher than the predetermined humidity, it is considered that the humidity sensitive membrane has deteriorated.

In the humidity measuring device 10 according to the present embodiment, in the case that the replacement determination unit 96 has determined that the dehumidifying device 38 has been replaced, and in the case that the measured humidity is greater than or equal to the second threshold value and less than the first threshold value, the correction unit 100 corrects the measured humidity and thereby obtains the corrected humidity. Consequently, even in the case that the humidity sensitive member is deteriorated, the humidity measuring device 10 is capable of maintaining the accuracy of the humidity of the gas.

In the humidity measuring device 10 according to the present embodiment, in the case that the replacement determination unit 96 has determined that the dehumidifying device 38 has been replaced, and in the case that the measured humidity of the temperature and humidity measurement unit 26 is greater than or equal to the first threshold value, the display control unit 52 controls the display device 54 to thereby cause there to be displayed on the display device 54 a display prompting the user to replace the temperature and humidity measurement unit 26. Consequently, in the case that the humidity sensitive membrane is severely deteriorated, the humidity measuring device 10 is capable of prompting the user to replace the temperature and humidity measurement unit 26.

Eighth Embodiment

Figure 22:
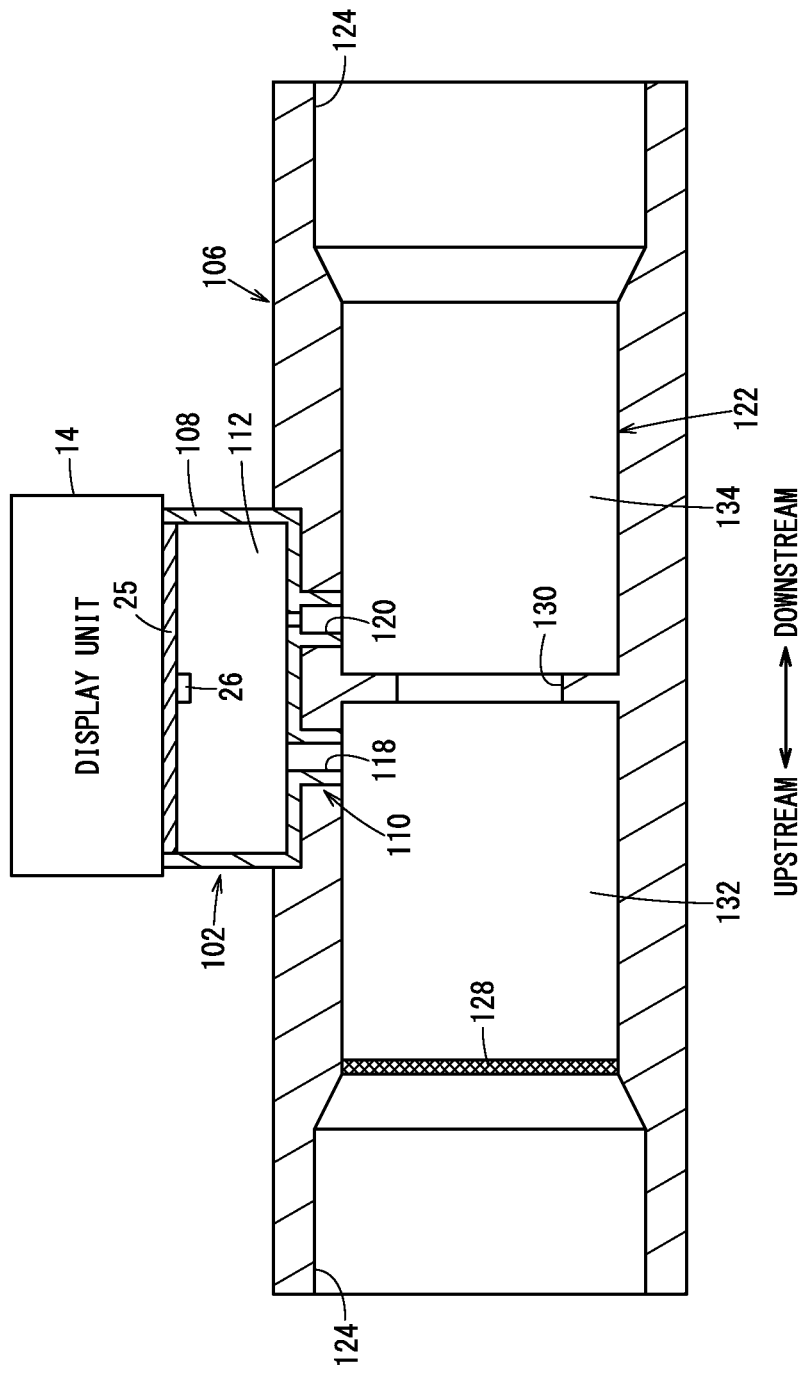
FIG. 22 is a view showing the humidity measuring device.
Figure 23:
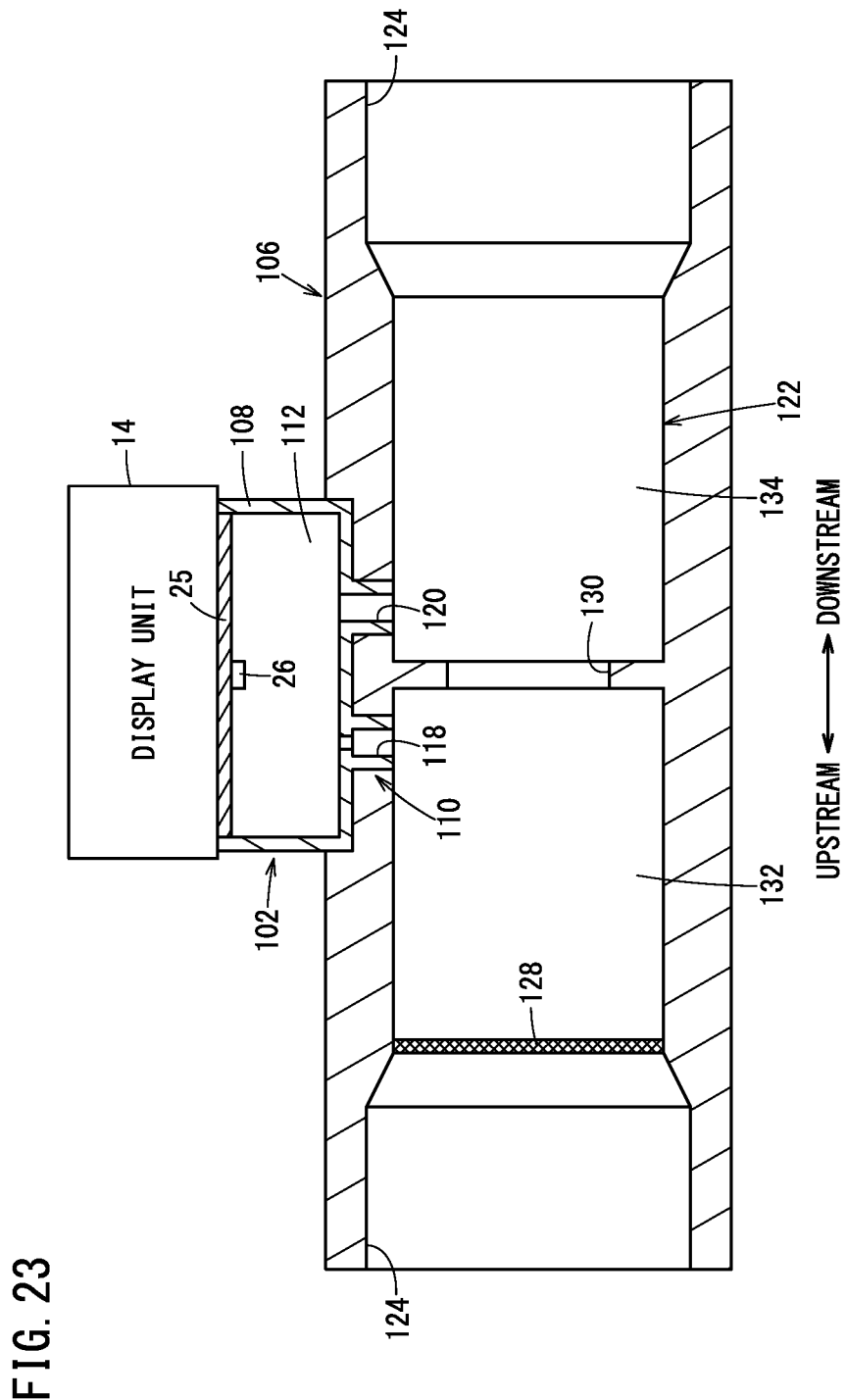
FIG. 23 is a view showing the humidity measuring device.

FIGS. 22 and 23 show the humidity measuring device 10. The humidity measuring device 10 includes a casing 102, the display unit 14, and a coupling member 106. Cross-sectional views of the casing 102 and the coupling member 106 are shown in FIGS. 22 and 23. A schematic diagram of the display unit 14 is shown in FIGS. 22 and 23.

The casing 102 includes a main body portion 108 and a connecting portion 110. The main body portion 108 includes an accommodating section 112 disposed in the interior of the main body portion 108. The accommodating section 112 is a space formed inside the main body portion 108.

The humidity measuring device 10 includes the electronic circuit board 25. The electronic circuit board 25 is arranged between the main body portion 108 and the display unit 14. A temperature and humidity measurement unit 26 is mounted on the electronic circuit board 25. The temperature and humidity measurement unit 26 is accommodated in the accommodating section 112. The temperature and humidity measurement unit 26 is an electronic component in which a temperature sensing element and a humidity sensing element are mounted in one single integrated circuit. The temperature sensing element measures the temperature of the gas in the accommodating section 112. The humidity sensing element measures the humidity of the gas in the accommodating section 112. The temperature and humidity measurement unit 26 outputs to the display unit 14 the temperature and humidity of the gas that were measured.

The connecting portion 110 includes a first connecting tube 118 and a second connecting tube 120. The first connecting tube 118 and the second connecting tube 120 are connected to the accommodating section 112. Further, the first connecting tube 118 and the second connecting tube 120 are connected to a coupling tube 122 of the coupling member 106, which will be described later. The gas flows in between the accommodating section 112 and the coupling tube 122 via the first connecting tube 118 and the second connecting tube 120. The cross-sectional area of the first connecting tube 118 and the cross-sectional area of the second connecting tube 120 are different. As shown in FIG. 22, the cross-sectional area of a minimum diameter portion of the second connecting tube 120 is smaller than the cross-sectional area of the minimum diameter portion of the first connecting tube 118. As shown in FIG. 23, the cross-sectional area of a minimum diameter portion of the first connecting tube 118 may be smaller than the cross-sectional area of the minimum diameter portion of the second connecting tube 120.

The coupling member 106 includes the coupling tube 122 and tube mounting members 124 in the interior of the coupling member 106. The coupling tube 122 is formed to extend in one direction. The tube mounting members 124 are connected respectively to both ends of the coupling tube 122. Each of the tube mounting members 124 opens to the exterior of the coupling member 106. The coupling member 106 is connected in the middle between tube portions 126 (see FIG. 24) through which the gas flows. The tube portions 126 are connected respectively to the tube mounting members 124. The coupling tube 122 is connected between the tube portion 126 and the tube portion 126. Consequently, via the coupling tube 122, the gas is capable of flowing between the tube portion 126 and the tube portion 126.

A filter 128 is mounted in the coupling tube 122. The filter 128 is arranged in the connecting portion between the coupling tube 122 and the tube mounting member 124 that is positioned on the upstream side with respect to the flow of the gas in the coupling tube 122. The coupling tube 122 includes an orifice 130. In the orifice 130, the cross-sectional area of a minimum diameter portion of the hole of the orifice 130 is smaller than the cross-sectional area of other locations of the coupling tube 122. The orifice 130 is arranged more downstream than the filter 128 with respect to the flow of the gas in the coupling tube 122. Hereinafter, within the coupling tube 122, the portion thereof located more upstream than the orifice 130 may be referred to as a first coupling chamber 132. Further, within the coupling tube 122, the portion thereof located more downstream than the orifice 130 may be referred to as a second coupling chamber 134.

The filter 128 is mounted on an end part of the upstream side of the coupling tube 122. Due to the filter 128, it becomes possible to remove foreign material mixed in the gas that flows into the coupling tube 122. Consequently, it is possible to prevent such foreign material from entering into the coupling tube 122.

In the first coupling chamber 132, the aforementioned first connecting tube 118 is connected to the coupling tube 122. Stated otherwise, the first connecting tube 118 is connected to the coupling tube 122 at a location between the filter 128 and the orifice 130, and at a more upstream location than the orifice 130, with respect to the flow of the gas in the coupling tube 122. In the second coupling chamber 134, the aforementioned second connecting tube 120 is connected to the coupling tube 122. Stated otherwise, the second connecting tube 120 is connected to the coupling tube 122 at a more downstream location than the orifice 130, with respect to the flow of the gas in the coupling tube 122.

Figure 24:
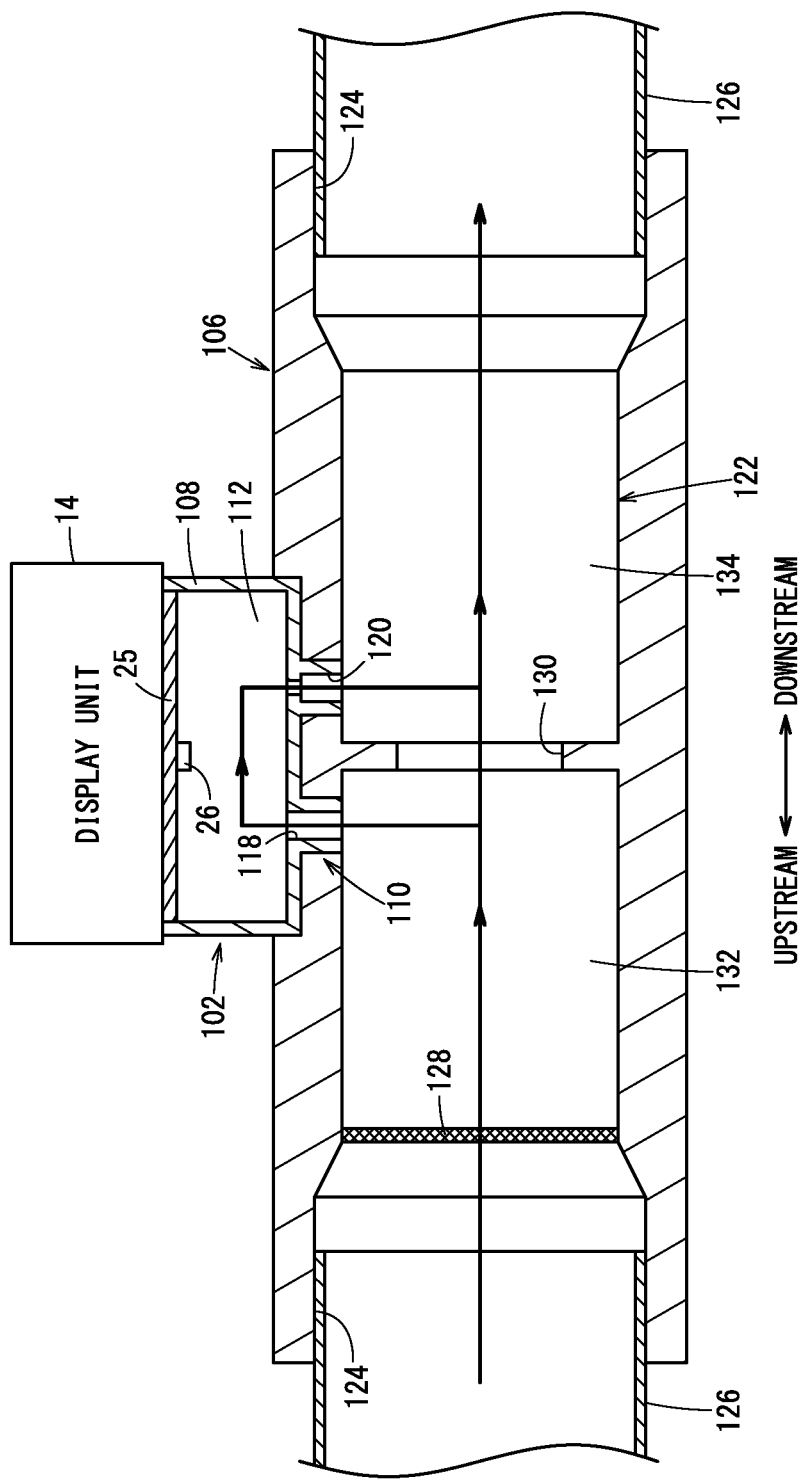
FIG. 24 is a diagram showing a state in which tube portions are connected to the humidity measuring device.

FIG. 24 is a diagram showing a state in which the tube portions 126 are connected to the humidity measuring device 10. The arrows in FIG. 24 indicate the flow of the gas.

Due to the orifice 130, the pressure in the first coupling chamber 132 becomes higher than the pressure in the second coupling chamber 134. Consequently, it becomes possible to allow the gas of the coupling tube 122 to flow from the first connecting tube 118 into the interior of the accommodating section 112. The cross-sectional area corresponding to the diameter of the second connecting tube 120 is smaller than the cross-sectional area corresponding to the diameter of the first connecting tube 118. Therefore, the pressure in the accommodating section 112 can be made substantially equivalent to the pressure in the first coupling chamber 132.

The gas flows into the accommodating section 112 after having passed through the filter 128. Therefore, it is possible to prevent foreign material from entering into the accommodating section 112.

The configuration of the display unit 14 is the same as the configuration of the display unit 14 of the first embodiment, the third embodiment, the fifth embodiment, the sixth embodiment, or the seventh embodiment.

Concerning the Accuracy in Measuring the Humidity

Figure 25:
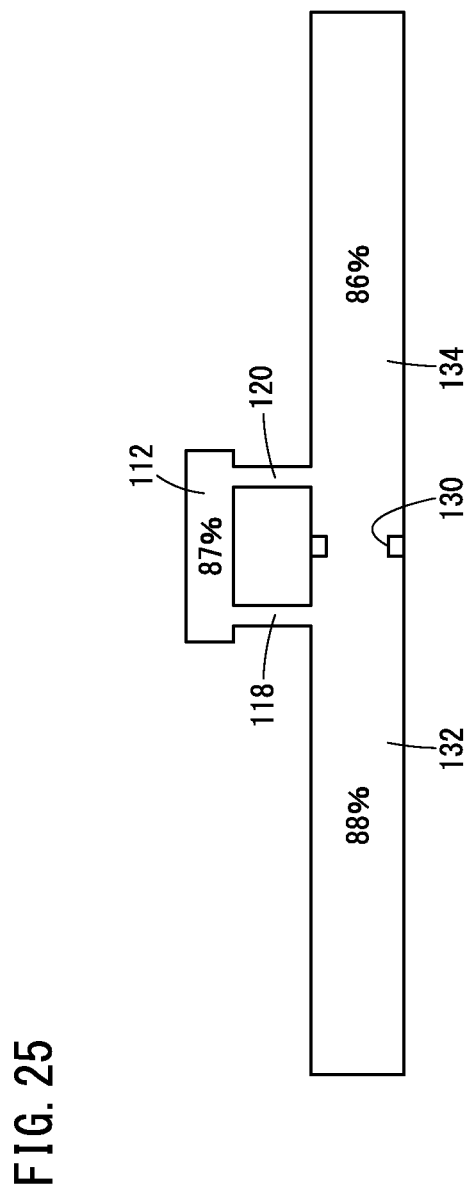
FIG. 25 shows a simulation result.
Figure 26:
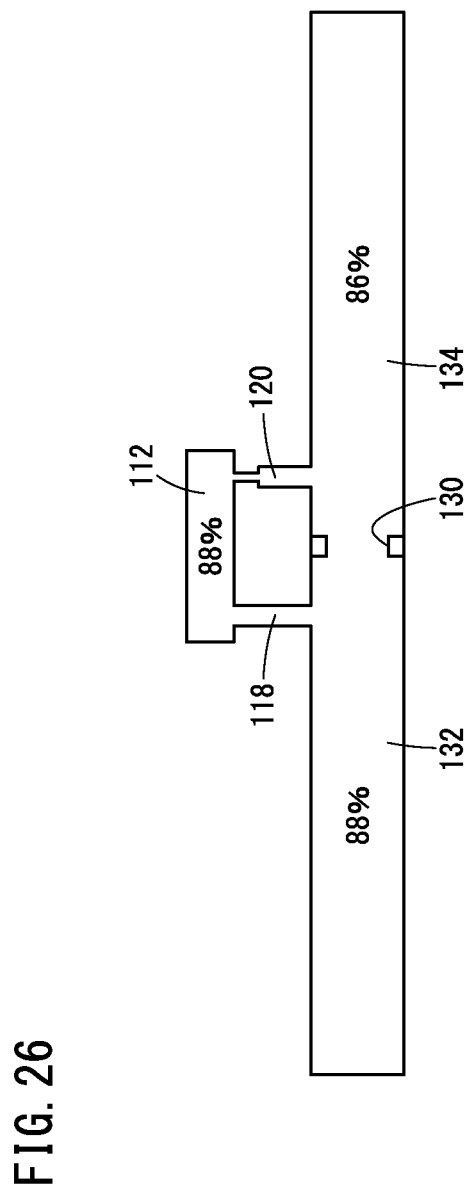
FIG. 26 shows a simulation result.
Figure 27:
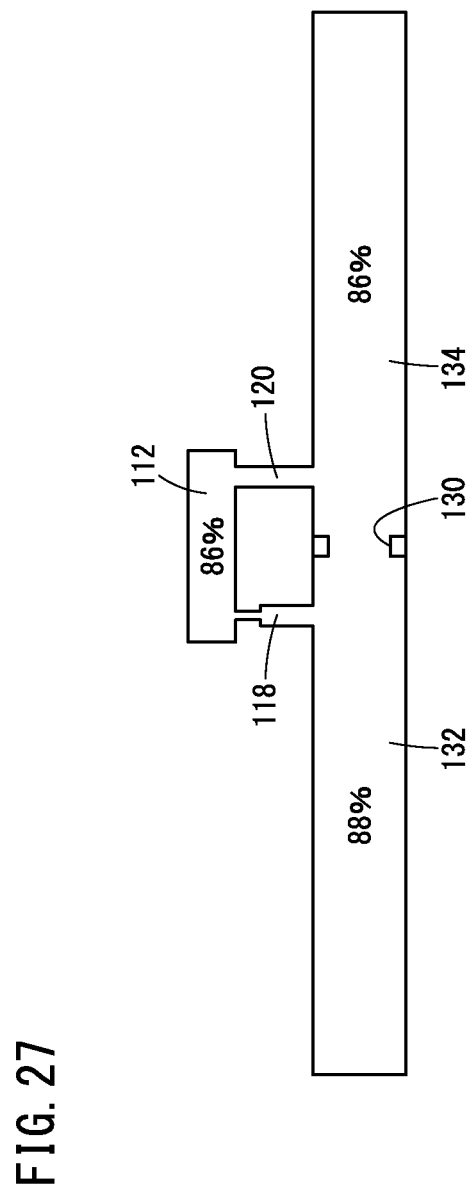
FIG. 27 shows a simulation result.

Using a computer, the present inventors performed simulations concerning the humidity in the first coupling chamber 132, the second coupling chamber 134, and the accommodating section 112. FIGS. 25, 26, and 27 are diagrams showing simulation results. FIG. 25 shows a simulation result for a case in which the cross-sectional area of a minimum diameter portion of the first connecting tube 118 and the cross-sectional area of a minimum diameter portion of the second connecting tube 120 are equivalent. FIG. 26 shows a simulation result for a case in which the cross-sectional area of the minimum diameter portion of the second connecting tube 120 is smaller than the cross-sectional area of the minimum diameter portion of the first connecting tube 118. FIG. 27 shows a simulation result for a case in which the cross-sectional area of the minimum diameter portion of the first connecting tube 118 is smaller than the cross-sectional area of the minimum diameter portion of the second connecting tube 120. In these simulations, a gas having a humidity of 88% was made to flow into the first coupling chamber 132.

In the case that the cross-sectional area of the minimum diameter portion of the first connecting tube 118 and the cross-sectional area of the minimum diameter portion of the second connecting tube 120 are equivalent, then as shown in FIG. 25, the humidity in the accommodating section 112 is lower than the humidity in the first coupling chamber 132. On the other hand, the humidity in the accommodating section 112 is higher than the humidity in the second coupling chamber 134. More specifically, the humidity in the accommodating section 112 differs from both the humidity in the first coupling chamber 132 and the humidity in the second coupling chamber 134. Therefore, although the temperature and humidity measurement unit 26 provided in the accommodating section 112 is capable of measuring the humidity of the gas that flows through the interior of the tube portions 126, the accuracy of such a measurement is low. Moreover, in this case, the pressure in the accommodating section 112 is lower than the pressure in the first coupling chamber 132. On the other hand, the pressure in the accommodating section 112 is higher than the pressure in the second coupling chamber 134.

In the case that the cross-sectional area of the minimum diameter portion of the second connecting tube 120 is smaller than the cross-sectional area of the minimum diameter portion of the first connecting tube 118, then as shown in FIG. 26, the humidity in the accommodating section 112 is substantially equivalent to the humidity in the first coupling chamber 132. On the other hand, the humidity in the accommodating section 112 is higher than the humidity in the second coupling chamber 134. Therefore, the temperature and humidity measurement unit 26 provided in the accommodating section 112 is capable of highly accurately measuring the humidity of the gas that flows through the interior of the tube portion 126 at a location more upstream than the orifice 130. Moreover, in this case, the pressure in the accommodating section 112 is substantially equivalent to the pressure in the first coupling chamber 132. On the other hand, the pressure in the accommodating section 112 is higher than the pressure in the second coupling chamber 134.

In the case that the cross-sectional area of the minimum diameter portion of the first connecting tube 118 is smaller than the cross-sectional area of the minimum diameter portion of the second connecting tube 120, then as shown in FIG. 27, the humidity in the accommodating section 112 is substantially equivalent to the humidity in the second coupling chamber 134. On the other hand, the humidity in the accommodating section 112 is lower than the humidity in the first coupling chamber 132. Therefore, the temperature and humidity measurement unit 26 provided in the accommodating section 112 is capable of highly accurately measuring the humidity of the gas that flows through the interior of the tube portion 126 at a location more downstream than the orifice 130. Moreover, in this case, the pressure in the accommodating section 112 is substantially equivalent to the pressure in the second coupling chamber 134. On the other hand, the pressure in the accommodating section 112 is lower than the pressure in the first coupling chamber 132.

Actions and Effects

The humidity measuring device 10 according to the present embodiment includes the coupling member 106 that is connected in the middle between the tube portions 126. The coupling tube 122 of the coupling member 106 and the accommodating section 112 of the casing 102 are connected by the first connecting tube 118 and the second connecting tube 120. The first connecting tube 118 is connected to the coupling tube 122 at a location upstream of the orifice 130. The second connecting tube 120 is connected to the coupling tube 122 at a location downstream of the orifice 130.

In accordance with these features, the gas flowing through the coupling tube 122 branches off and flows in a diverted manner, and is delivered from the first connecting tube 118 into the accommodating section 112. Therefore, the temperature and humidity measurement unit 26 is capable of measuring the humidity of the gas in the accommodating section 112, under the same pressure as in the tube portions 126. As a result, the humidity measuring device 10 is capable of measuring the humidity of the gas that flows through the tube portions 126. Further, it is possible to prevent water droplets or the like, which are mixed in the gas that flows through the tube portions 126, from entering into the accommodating section 112. As a result, it is possible to prevent the temperature and humidity measurement unit 26 from becoming contaminated.

Further, in the humidity measuring device 10 according to the present embodiment, the gas that flows through the tube portions 126 flows from the coupling tube 122, through the first connecting tube 118, and into the accommodating section 112. The gas that has flowed into the accommodating section 112 passes through the second connecting tube 120, and is returned to the coupling tube 122. Therefore, the gas that flows through the tube portions 126 is not discharged to the exterior. As a result, a decrease in the gas can be suppressed.

In the humidity measuring device 10 according to the present embodiment, the cross-sectional area of the first connecting tube 118 and the cross-sectional area of the second connecting tube 120 differ from each other. In the case that the cross-sectional area of the minimum diameter portion of the second connecting tube 120 is made smaller than the cross-sectional area of the minimum diameter portion of the first connecting tube 118, the temperature and humidity measurement unit 26 is capable of highly accurately measuring the humidity of the gas that flows through the interior of the tube portion 126 at the location more upstream than the orifice 130. In the case that the cross-sectional area of the minimum diameter portion of the first connecting tube 118 is made smaller than the cross-sectional area of the minimum diameter portion of the second connecting tube 120, the temperature and humidity measurement unit 26 is capable of highly accurately measuring the humidity of the gas that flows through the interior of the tube portion 126 at the location more downstream than the orifice 130.

Ninth Embodiment

Figure 28:
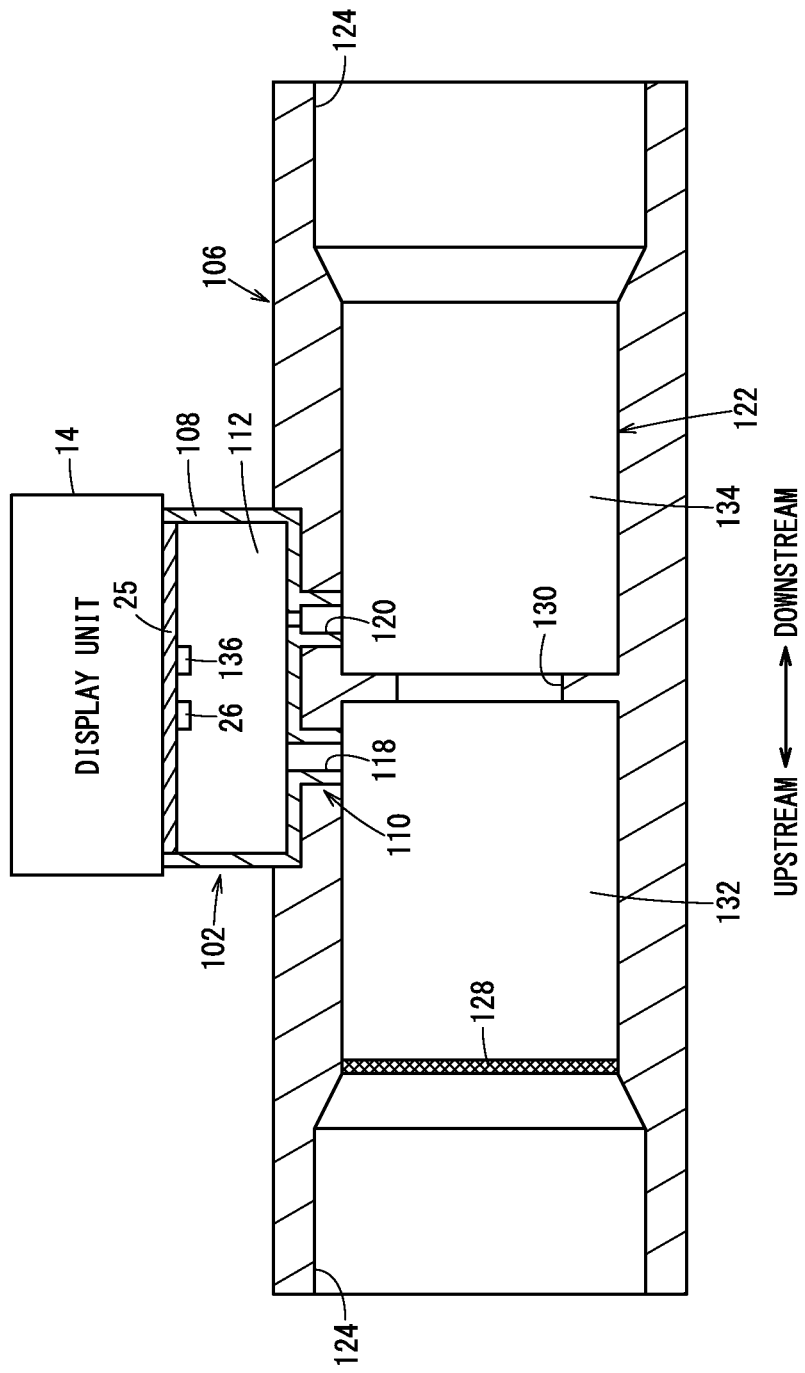
FIG. 28 is a view showing the humidity measuring device.

FIG. 28 shows the humidity measuring device 10. The humidity measuring device 10 includes the casing 102, the display unit 14, and the coupling member 106. In FIG. 28, cross-sectional views of the casing 102 and the coupling member 106 are shown. In FIG. 28, a schematic diagram of the display unit 14 is shown.

A flow sensor 136 is attached to the electronic circuit board 25. The flow sensor 136 is accommodated in the accommodating section 112 of the casing 102. The flow sensor 136 detects the flow rate of the gas that flows through the accommodating section 112. The flow rate of the gas that flows through the tube portions 126 can be obtained from the flow rate of the gas that flows through the accommodating section 112. The flow sensor 136 is constituted from a sensor, a thermistor, and platinum or the like. The sensor is constituted by a MEMS (Micro Electro Mechanical System). Concerning other constituent features of the humidity measuring device 10 according to the present embodiment, they are the same as those of the humidity measuring device 10 according to the eighth embodiment.

Actions and Effects

In the humidity measuring device 10 according to the present embodiment, the flow sensor 136 is accommodated in the accommodating section 112 of the casing 102. Consequently, the flow rate of the gas that flows through the tube portions 126 can be obtained.

Tenth Embodiment

FIG. 29 shows the humidity measuring device 10. The humidity measuring device 10 includes the casing 102, the display unit 14, and the coupling member 106. In FIG. 29, a cross-sectional view of the casing 102 and the coupling member 106 is shown. In FIG. 29, a schematic diagram of the display unit 14 is shown.

The filter 128 and a filter 138 are mounted in the coupling tube 122. The filter 138 is arranged on an opposite side from the filter 128 with the orifice 130 being interposed therebetween. The filter 128 is mounted in a connecting portion between the coupling tube 122 and one of the tube mounting members 124. The filter 138 is mounted in a connecting portion between the coupling tube 122 and another one of the tube mounting members 124.

The filter 128 is mounted on one end of the coupling tube 122, and the filter 138 is mounted on another end of the coupling tube 122. In accordance with these features, even in the case that the direction in which the gas flows is switched, by the filter 128 or the filter 138, it is still possible to remove foreign material mixed in the gas that flows into the coupling tube 122. Consequently, it is possible to prevent such foreign material from entering into the coupling tube 122.

In should be noted that the present invention is not limited to the embodiments described above, and various additional or modified configurations could be adopted therein without departing from the essence and gist of the present invention.

Technical Concepts Obtained from the Embodiments

The technical concepts that can be grasped from the above-described embodiments will be described below.

The present invention is characterized by the humidity measuring device (10) configured to measure the humidity of the gas, including the measurement unit (26) including the temperature sensing element configured to measure temperature, and the humidity sensing element configured to measure humidity, the casing (12) including the accommodating section (20) in which the measurement unit is accommodated, and the display unit (14) including the display device (54), and which is fixed to the casing, wherein the display unit further includes the display control unit (52) configured to control the display device to thereby cause the display device to display at least one of the humidity of the gas measured by the humidity sensing element, or the dew point temperature of the gas calculated based on both the temperature of the gas measured by the temperature sensing element and the humidity of the gas measured by the humidity sensing element. In accordance with these features, the user is capable of confirming at least one of the humidity of the gas or the dew point temperature of the gas, at the location where the humidity measuring device is installed.

In the above-described humidity measuring device, the display unit may include the first output unit (44) configured to output to the external device (46) on the external portion of the humidity measuring device at least one of the comparison result of comparing the dew point temperature of the gas with the set dew point temperature, or the comparison result of comparing the humidity of the gas with the set humidity. In accordance with these features, the humidity measuring device is capable of outputting to the external device at least one of the comparison result between the dew point temperature of the gas and the set dew point temperature, or the comparison result between the humidity of the gas and the set humidity.

In the above-described humidity measuring device, the display unit may include the second output unit (48) configured to output to the external device (50) on the external portion of the humidity measuring device at least one of the dew point temperature of the gas, or the humidity of the gas. In accordance with this feature, the humidity measuring device is capable of outputting to the external device on the external portion of the humidity measuring device at least one of the dew point temperature of the gas, or the humidity of the gas.

In the above-described humidity measuring device, the casing may include the supply tube (22) configured to supply the gas at a measurement location where the humidity of the gas is measured into the accommodating section, and the discharge tube (24) configured to discharge the gas from the accommodating section into the atmosphere, wherein the supply tube and the discharge tube are connected to the accommodating section, in a manner so that a direction in which the gas flows inwardly from the supply tube to the accommodating section, and a direction in which the gas flows outwardly from the accommodating section to the discharge tube are positioned on different straight lines. In accordance with these features, the humidity measuring device is capable of improving the accuracy in measuring the humidity of the gas.

In the above-described humidity measuring device, the casing may include the connecting tube (28) configured to connect the measurement location and the supply tube to enable the gas to flow between the measurement location and the supply tube, the filter (32) may be mounted in the connecting tube, the connecting tube may include the orifice (30), the orifice may be arranged more on a side of the accommodating section than the filter, and the orifice may be formed in a manner so that the cross-sectional area of the hole of the orifice is smaller than the cross-sectional area of the discharge tube. In accordance with these features, the pressure of the gas inside the accommodating section can be made equivalent to the atmospheric pressure.

In the above-described humidity measuring device, the display unit may include the pressure input unit (94) configured to input the pressure of the gas at the measurement location, and the dew point temperature calculation unit (40) configured to calculate the dew point temperature under pressure as the dew point temperature, based on the temperature of the gas measured by the temperature sensing element, the humidity of the gas measured by the humidity sensing element, and the pressure of the gas input by the pressure input unit. In accordance with these features, since the measurement unit does not come into contact with the high pressure gas, the adherence of water droplets to the measurement unit is suppressed.

In the above-described humidity measuring device, there may further be included the pressure measurement unit (76) configured to measure the pressure of the gas at the measurement location, and the display unit may include the dew point temperature calculation unit configured to calculate the dew point temperature under pressure as the dew point temperature, based on the temperature of the gas measured by the temperature sensing element, the humidity of the gas measured by the humidity sensing element, and the pressure of the gas measured by the pressure measurement unit. In accordance with these features, since the measurement unit does not come into contact with the high pressure gas, the adherence of water droplets to the measurement unit is suppressed.

In the above-described humidity measuring device, the casing may include the connecting tube configured to connect the measurement location and the supply tube to enable the gas to flow between the measurement location and the supply tube, the filter may be installed in the connecting tube, the discharge tube may include the orifice (70), and the orifice may be formed so that the cross-sectional area of the hole of the orifice is smaller than the cross-sectional area of the supply tube. In accordance with these features, the humidity measuring device is capable of filling the interior of the accommodating section with the compressed gas.

In the above-described humidity measuring device, the filter may be made of metal. In accordance with this feature, the humidity measuring device is capable of improving the accuracy in measuring the humidity of the gas.

In the above-described humidity measuring device, the casing may include the main body portion (16) including the supply tube, and the connecting portion (18) including the connecting tube, and in a state in which the filter is installed in the connecting portion, the connecting portion may be attached to the main body portion in a manner so that the connecting portion is detachable from the main body portion. In accordance with these features, the user is capable of easily carrying out replacement of the filter of the humidity measuring device.

In the above-described humidity measuring device, the gas at the measurement location where the humidity of the gas is measured may be a gas that is discharged from the dehumidifying device (38) configured to dehumidify the gas, and the display unit may include the replacement determination unit (96) configured to determine whether or not the dehumidifying device has been replaced, and the correction unit (100) which, in the case that the humidity of the gas measured by the humidity sensing element is higher than a threshold value immediately after having determined that the dehumidifying device has been replaced, thereafter is configured to correct the humidity of the gas measured by the humidity sensing element, based on the humidity of the gas measured by the humidity sensing element immediately after having determined that the dehumidifying device has been replaced, and the dehumidifying capability of the dehumidifying device that has been replaced. Even in the case that the humidity sensitive membrane is deteriorated, the humidity measuring device is capable of maintaining the accuracy of the humidity of the gas.

In the above-described humidity measuring device, the gas at the measurement location where the humidity of the gas is measured may be a gas that is discharged from the dehumidifying device configured to dehumidify the gas, and the display unit may include the replacement determination unit configured to determine whether or not the dehumidifying device has been replaced, and in the case that the humidity of the gas measured by the humidity sensing element is higher than a threshold value immediately after having determined that the dehumidifying device has been replaced, the display control unit may control the display unit to thereby cause a display to be displayed on the display device, the display prompting the user to replace the measurement unit. In accordance with these features, in the case that the humidity sensitive membrane is severely deteriorated, the humidity measuring device is capable of prompting the user to replace the measurement unit.

In the above-described humidity measuring device, the coupling member (106) may be connected in the middle between the tube portions (126) through which the gas flows, the coupling member may include the coupling tube (122) configured to connect one of the tube portions and another of the tube portions, and which enables the gas to flow between the one tube portion and the other tube portion, the filter (128) may be mounted in the coupling tube, the coupling tube may include the orifice (130), with respect to the flow of the gas in the coupling tube, the orifice may be arranged at a location more downstream than the filter, the casing may include the first tube (118) and the second tube (120) configured to connect the coupling tube and the accommodating section, and which enable the gas to flow between the coupling tube and the accommodating section, with respect to the flow of the gas in the coupling tube, the first tube is connected to the coupling tube at a location more upstream than the orifice, and between the filter and the orifice, and with respect to the flow of the gas in the coupling tube, the second tube is connected to the coupling tube at a location more downstream than the orifice. In accordance with these features, the humidity measuring device is capable of highly accurately measuring the humidity of the gas that flows through the tube portions.

In the above-described humidity measuring device, the cross-sectional area of the first tube and the cross-sectional area of the second tube may be different. In accordance with this feature, the humidity measuring device is capable of highly accurately measuring the humidity of the gas that flows through the tube portions.

In the above-described humidity measuring device, there may further be included the flow sensor (136) configured to measure the flow rate of the gas, wherein the flow sensor may be accommodated in the accommodating section. In accordance with this feature, the humidity measuring device is capable of determining the flow rate of the gas that flows through the tube portions.

What is claimed is:

1. A humidity measuring device configured to measure humidity of a gas, the humidity measuring device comprising:
    a measurement unit including a temperature sensing element configured to measure temperature, and a humidity sensing element configured to measure humidity;
    a casing including an accommodating section in which the measurement unit is accommodated; and
    a display unit including a display device, and which is fixed to the casing,
    wherein the display unit further comprises a display control unit configured to control the display device to thereby cause the display device to display at least one of the humidity of the gas measured by the humidity sensing element, or a dew point temperature of the gas calculated based on both the temperature of the gas measured by the temperature sensing element and the humidity of the gas measured by the humidity sensing element,
    wherein the casing comprises:
    a supply tube configured to supply the gas at a measurement location where the humidity of the gas is measured into the accommodating section;
    a discharge tube configured to discharge the gas from the accommodating section into atmosphere;
    a connecting tube configured to connect the measurement location and the supply tube to enable the gas to flow between the measurement location and the supply tube;
    a main body portion including the supply tube; and
    a connecting portion including the connecting tube, wherein the supply tube and the discharge tube are connected to the accommodating section, in a manner so that a direction in which the gas flows inwardly from the supply tube to the accommodating section, and a direction in which the gas flows outwardly from the accommodating section to the discharge tube are positioned on different straight lines, a filter is mounted in the connecting tube, the connecting tube includes an orifice, the orifice is arranged more on a side of the accommodating section than the filter, the orifice is formed in a manner so that a cross-sectional area of a hole of the orifice is smaller than a cross-sectional area of the discharge tube, and in a state in which the filter is installed in the connecting portion, the connecting portion is attached to the main body portion in a manner so that the connecting portion is detachable from the main body portion.

2. The humidity measuring device according to claim 1, wherein the display unit includes a first output unit configured to output to an external device on an external portion of the humidity measuring device at least one of a comparison result of comparing the dew point temperature of the gas with a set dew point temperature, or a comparison result of comparing the humidity of the gas with a set humidity.

3. The humidity measuring device according to claim 1, wherein the display unit includes a second output unit configured to output to an external device on an external portion of the humidity measuring device at least one of the dew point temperature of the gas, or the humidity of the gas.

4. The humidity measuring device according to claim 1, wherein the display unit comprises:
a pressure input unit configured to input a pressure of the gas at the measurement location; and
a dew point temperature calculation unit configured to calculate the dew point temperature under pressure as the dew point temperature, based on the temperature of the gas measured by the temperature sensing element, the humidity of the gas measured by the humidity sensing element, and the pressure of the gas input by the pressure input unit.

5. The humidity measuring device according to claim 1, further comprising a pressure measurement unit configured to measure a pressure of the gas at the measurement location,
wherein the display unit comprises a dew point temperature calculation unit configured to calculate the dew point temperature under pressure as the dew point temperature, based on the temperature of the gas measured by the temperature sensing element, the humidity of the gas measured by the humidity sensing element, and the pressure of the gas measured by the pressure measurement unit.

6. The humidity measuring device according to claim 1, wherein the filter is made of metal.

7. A humidity measuring device configured to measure humidity of a gas, the humidity measuring device comprising:
a measurement unit including a temperature sensing element configured to measure temperature, and a humidity sensing element configured to measure humidity;
a casing including an accommodating section in which the measurement unit is accommodated; and
a display unit including a display device, and which is fixed to the casing, wherein:

the gas at the measurement location where the humidity of the gas is measured is the gas that is discharged from a dehumidifying device configured to dehumidify the gas; and the display unit comprises:
a display control unit configured to control the display device to thereby cause the display device to display at least one of the humidity of the gas measured by the humidity sensing element, or a dew point temperature of the gas calculated based on both the temperature of the gas measured by the temperature sensing element and the humidity of the gas measured by the humidity sensing element,
a replacement determination unit configured to determine whether or not the dehumidifying device has been replaced; and
a correction unit which, in a case that the humidity of the gas measured by the humidity sensing element is higher than a threshold value immediately after having determined that the dehumidifying device has been replaced, thereafter, is configured to correct the humidity of the gas measured by the humidity sensing element, based on the humidity of the gas measured by the humidity sensing element immediately after having determined that the dehumidifying device has been replaced, and a dehumidifying capability of the dehumidifying device that has been replaced.

8. A humidity measuring device configured to measure humidity of a gas, the humidity measuring device comprising:
a measurement unit including a temperature sensing element configured to measure temperature, and a humidity sensing element configured to measure humidity;
a casing including an accommodating section in which the measurement unit is accommodated; and
a display unit including a display device, and which is fixed to the casing, wherein:
the gas at the measurement location where the humidity of the gas is measured is the gas that is discharged from a dehumidifying device configured to dehumidify the gas; and
the display unit comprises:
a display control unit configured to control the display device to thereby cause the display device to display at least one of the humidity of the gas measured by the humidity sensing element, or a dew point temperature of the gas calculated based on both the temperature of the gas measured by the temperature sensing element and the humidity of the gas measured by the humidity sensing element; and
a replacement determination unit configured to determine whether or not the dehumidifying device has been replaced,
wherein in a case that the humidity of the gas measured by the humidity sensing element is higher than a threshold value immediately after having determined that the dehumidifying device has been replaced, the display control unit controls the display unit to thereby cause a display to be displayed on the display device, the display prompting the user to replace the measurement unit.

9. A humidity measuring device configured to measure humidity of a gas, the humidity measuring device comprising:
a measurement unit including a temperature sensing element configured to measure temperature, and a humidity sensing element configured to measure humidity;

a casing including an accommodating section in which the measurement unit is accommodated; and a display unit including a display device, and which is fixed to the casing; and a coupling member connected in the middle between tube portions through which the gas flows, wherein:

the display unit further comprises a display control unit configured to control the display device to thereby cause the display device to display at least one of the humidity of the gas measured by the humidity sensing element, or a dew point temperature of the gas calculated based on both the temperature of the gas measured by the temperature sensing element and the humidity of the gas measured by the humidity sensing element;

the coupling member includes a coupling tube configured to connect one of the tube portions and another of the tube portions, and which enables the gas to flow between the one tube portion and the other tube portion;

a filter is mounted in the coupling tube;

the coupling tube includes an orifice;

with respect to the flow of the gas in the coupling tube, the orifice is arranged at a location more downstream than the filter;

the casing includes a first tube and a second tube configured to connect the coupling tube and the accommodating section, and to enable the gas to flow between the coupling tube and the accommodating section;

with respect to the flow of the gas in the coupling tube, the first tube is connected to the coupling tube at a location more upstream than the orifice, and between the filter and the orifice; and with respect to a flow of the gas in the coupling tube, the second tube is connected to the coupling tube at a location more downstream than the orifice.

10. The humidity measuring device according to claim 9, wherein a cross-sectional area of the first tube and a cross-sectional area of the second tube are different.

11. The humidity measuring device according to claim 9, further comprising a flow sensor configured to measure a flow rate of the gas, wherein the flow sensor is accommodated in the accommodating section.

* * * * *